United States Patent
Gross et al.

(10) Patent No.: US 9,125,732 B2
(45) Date of Patent: Sep. 8, 2015

(54) DEVICES AND METHODS FOR CONTROL OF BLOOD PRESSURE

(75) Inventors: Yossi Gross, Moshav Mazor (IL); Itzik Avneri, Tel Aviv (IL); Ori Weisberg, Shderna (IL); Moshe Eshkol, Harulzim (IL)

(73) Assignee: VASCULAR DYNAMICS, INC., Mountain View, CA (US)

( * ) Notice: Subject to any disclaimer, the term of this patent is extended or adjusted under 35 U.S.C. 154(b) by 0 days.

(21) Appl. No.: 13/030,384

(22) Filed: Feb. 18, 2011

(65) Prior Publication Data

US 2011/0178416 A1 Jul. 21, 2011

Related U.S. Application Data

(63) Continuation-in-part of application No. 12/774,254, filed on May 5, 2010, now abandoned, which is a continuation-in-part of application No. 12/602,787, filed as application No. PCT/IL2009/000932 on Sep. 29, 2009.

(60) Provisional application No. 61/194,339, filed on Sep. 26, 2008.

(51) Int. Cl.
*A61F 2/82* (2013.01)
*A61F 2/06* (2013.01)
*A61F 2/86* (2013.01)

(52) U.S. Cl.
CPC ... *A61F 2/06* (2013.01); *A61F 2/82* (2013.01); *A61F 2/86* (2013.01); *A61F 2002/825* (2013.01); *A61F 2230/0019* (2013.01)

(58) Field of Classification Search
CPC .............................................. A61F 2002/068
USPC ...................................... 623/1.15, 1.24, 1.26
See application file for complete search history.

(56) References Cited

U.S. PATENT DOCUMENTS

| 3,650,277 A | 3/1972 | Sjostrand et al. |
| 4,201,219 A | 5/1980 | Bozal |

(Continued)

FOREIGN PATENT DOCUMENTS

| EP | 0791341 | 8/1997 |
| EP | 1 127 557 | 8/2001 |

(Continued)

OTHER PUBLICATIONS

J.H.P. Lardenoye, et al., "Inhibition of Accelerated Atherosclerosis in Vein Grafts by Placement of External Stent in ApoE*3-Leiden Transgenic Mice", Arteriosclerosis, Thrombosis, and Vascular Biology. 2002; 22:1433.) © 2002.

(Continued)

*Primary Examiner* — Thomas J Sweet
*Assistant Examiner* — Megan Wolf
(74) *Attorney, Agent, or Firm* — Wilson Sonsini Goodrich & Rosati

(57) ABSTRACT

Apparatus and methods are described including an implantable device shaped to define (a) at least two artery-contact regions, the artery-contact regions comprising struts that are configured to stretch an arterial wall by applying pressure to the arterial wall, and (b) at least two crimping regions that comprise locking mechanisms configured to prevent the crimping regions from becoming crimped due to pressure from the wall of the artery on the artery-contact regions. The crimping regions are configured to be crimped during insertion of the device, via a catheter, by the locking mechanisms being unlocked during insertion of the device. Other embodiments are also described.

15 Claims, 16 Drawing Sheets

(56) References Cited

U.S. PATENT DOCUMENTS

| | | |
|---|---|---|
| 4,791,931 A | 12/1988 | Slate |
| 4,830,003 A | 5/1989 | Wolff et al. |
| 4,887,613 A | 12/1989 | Farr et al. |
| 4,938,766 A | 7/1990 | Jarvik |
| 5,403,341 A | 4/1995 | Solar |
| 5,437,285 A | 8/1995 | Verrier |
| 5,458,626 A | 10/1995 | Krause |
| 5,630,829 A | 5/1997 | Lauterjung |
| 5,669,924 A | 9/1997 | Shaknovich |
| 5,707,400 A | 1/1998 | Terry, Jr. et al. |
| 5,727,558 A | 3/1998 | Hakki |
| 5,792,155 A * | 8/1998 | Van Cleef ............ 606/158 |
| 6,013,085 A | 1/2000 | Howard |
| 6,086,527 A | 7/2000 | Talpade |
| 6,306,141 B1 | 10/2001 | Jervis |
| 6,322,553 B1 | 11/2001 | Vito |
| 6,375,666 B1 | 4/2002 | Mische |
| 6,413,273 B1 | 7/2002 | Baum |
| 6,442,424 B1 | 8/2002 | Ben-Haim |
| 6,520,987 B1 | 2/2003 | Plante |
| 6,522,926 B1 | 2/2003 | Kieval |
| 6,554,856 B1 | 4/2003 | Doorly et al. |
| 6,575,994 B1 | 6/2003 | Marin et al. |
| 6,616,624 B1 | 9/2003 | Kieval |
| 6,641,605 B1 | 11/2003 | Stergiopulos |
| 6,669,686 B1 | 12/2003 | Singh |
| 6,681,136 B2 | 1/2004 | Schuler |
| 6,764,498 B2 | 7/2004 | Mische |
| 6,850,801 B2 | 2/2005 | Kieval |
| 6,899,669 B2 | 5/2005 | Vito |
| 6,957,106 B2 | 10/2005 | Schuler |
| 6,972,031 B1 | 12/2005 | Braginsky et al. |
| 6,974,445 B2 | 12/2005 | Stergiopulos |
| 6,985,774 B2 | 1/2006 | Kieval |
| 7,008,446 B1 * | 3/2006 | Amis et al. ............ 623/1.21 |
| 7,044,981 B2 | 5/2006 | Liu et al. |
| 7,060,080 B2 | 6/2006 | Bachmann |
| 7,094,254 B2 | 8/2006 | Stergiopulos |
| 7,128,750 B1 | 10/2006 | Stergiopulos |
| 7,158,832 B2 | 1/2007 | Kieval |
| 7,159,593 B2 | 1/2007 | McCarthy et al. |
| 7,194,313 B2 | 3/2007 | Libbus |
| 7,201,772 B2 | 4/2007 | Schwammenthal |
| 7,218,964 B2 | 5/2007 | Hill et al. |
| 7,238,191 B2 | 7/2007 | Bachmann |
| 7,270,675 B2 | 9/2007 | Chun |
| 7,300,449 B2 | 11/2007 | Mische |
| 7,331,987 B1 | 2/2008 | Cox |
| 7,373,204 B2 | 5/2008 | Gelfand et al. |
| 7,381,222 B2 | 6/2008 | Pflueger et al. |
| 7,389,149 B2 | 6/2008 | Rossing |
| 7,395,119 B2 | 7/2008 | Hagen |
| 7,491,229 B2 | 2/2009 | Eder |
| 7,530,995 B2 | 5/2009 | Quijano et al. |
| 7,625,400 B2 | 12/2009 | Bowe |
| 7,628,803 B2 | 12/2009 | Pavcnik et al. |
| 7,637,937 B2 | 12/2009 | Case et al. |
| 7,647,931 B2 | 1/2010 | Pflueger |
| 8,361,140 B2 * | 1/2013 | Meyer et al. ............ 623/1.15 |
| 8,923,972 B2 | 12/2014 | Gross |
| 2001/0003801 A1 | 6/2001 | Strecker |
| 2002/0035392 A1 | 3/2002 | Wilson |
| 2002/0173838 A1 | 11/2002 | Frazier |
| 2003/0060585 A1 | 3/2003 | Radhakrishnan et al. |
| 2003/0060858 A1 | 3/2003 | Kieval |
| 2003/0199806 A1 | 10/2003 | Kieval |
| 2004/0010303 A1 | 1/2004 | Bolea |
| 2004/0019364 A1 | 1/2004 | Kieval |
| 2004/0106976 A1 | 6/2004 | Bailey et al. |
| 2004/0111006 A1 | 6/2004 | Alferness et al. |
| 2004/0149294 A1 | 8/2004 | Gianchandani et al. |
| 2004/0193092 A1 | 9/2004 | Deal |
| 2004/0249442 A1 | 12/2004 | Fleming et al. |
| 2004/0254616 A1 | 12/2004 | Rossing |
| 2005/0027346 A1 | 2/2005 | Arkusz et al. |
| 2005/0033407 A1 | 2/2005 | Weber et al. |
| 2005/0090894 A1 * | 4/2005 | Pazienza et al. ............ 623/1.15 |
| 2005/0096710 A1 | 5/2005 | Kieval |
| 2005/0143765 A1 | 6/2005 | Bachmann |
| 2005/0143766 A1 | 6/2005 | Bachmann |
| 2005/0143785 A1 | 6/2005 | Libbus |
| 2005/0149128 A1 | 7/2005 | Heil, Jr. |
| 2005/0149131 A1 | 7/2005 | Libbus |
| 2005/0149143 A1 | 7/2005 | Libbus |
| 2005/0154418 A1 | 7/2005 | Kieval et al. |
| 2005/0203610 A1 | 9/2005 | Tzeng |
| 2005/0232965 A1 | 10/2005 | Falotico |
| 2005/0251212 A1 | 11/2005 | Kieval |
| 2005/0261257 A1 | 11/2005 | Vermeer |
| 2006/0004417 A1 | 1/2006 | Rossing |
| 2006/0004420 A1 | 1/2006 | Rossing |
| 2006/0004430 A1 | 1/2006 | Rossing |
| 2006/0074453 A1 | 4/2006 | Kieval et al. |
| 2006/0089678 A1 | 4/2006 | Shalev |
| 2006/0111626 A1 | 5/2006 | Rossing |
| 2006/0217588 A1 | 9/2006 | Gross et al. |
| 2006/0241334 A1 | 10/2006 | Dubi |
| 2006/0253193 A1 * | 11/2006 | Lichtenstein et al. ......... 623/3.1 |
| 2006/0265038 A1 | 11/2006 | Hagen |
| 2006/0276852 A1 | 12/2006 | Demarais |
| 2006/0293712 A1 | 12/2006 | Kieval |
| 2007/0021790 A1 | 1/2007 | Kieval |
| 2007/0021792 A1 | 1/2007 | Kieval |
| 2007/0021794 A1 | 1/2007 | Kieval |
| 2007/0021796 A1 | 1/2007 | Kieval |
| 2007/0021797 A1 | 1/2007 | Kieval |
| 2007/0021798 A1 | 1/2007 | Kieval |
| 2007/0021799 A1 | 1/2007 | Kieval |
| 2007/0038255 A1 | 2/2007 | Kieval |
| 2007/0038259 A1 | 2/2007 | Kieval |
| 2007/0038260 A1 | 2/2007 | Kieval |
| 2007/0038261 A1 | 2/2007 | Kieval |
| 2007/0038262 A1 | 2/2007 | Kieval |
| 2007/0049989 A1 | 3/2007 | Rossing |
| 2007/0055296 A1 | 3/2007 | Stergiopulos |
| 2007/0060972 A1 | 3/2007 | Kieval |
| 2007/0100433 A1 | 5/2007 | Limon |
| 2007/0106340 A1 | 5/2007 | Bolea |
| 2007/0142879 A1 | 6/2007 | Greenberg |
| 2007/0156167 A1 | 7/2007 | Connors et al. |
| 2007/0156198 A1 | 7/2007 | Rossing |
| 2007/0156201 A1 | 7/2007 | Rossing |
| 2007/0167984 A1 | 7/2007 | Kieval |
| 2007/0185542 A1 | 8/2007 | Bolea |
| 2007/0185543 A1 | 8/2007 | Rossing |
| 2007/0187255 A1 | 8/2007 | Ogasawara |
| 2007/0198082 A1 | 8/2007 | Kapadia et al. |
| 2007/0250085 A1 | 10/2007 | Bachmann |
| 2007/0276442 A1 | 11/2007 | Hagen |
| 2007/0276459 A1 | 11/2007 | Rossing |
| 2007/0282385 A1 | 12/2007 | Rossing |
| 2007/0287879 A1 * | 12/2007 | Gelbart et al. ............ 600/16 |
| 2008/0004673 A1 | 1/2008 | Rossing |
| 2008/0009916 A1 | 1/2008 | Rossing |
| 2008/0009917 A1 | 1/2008 | Rossing |
| 2008/0027469 A1 | 1/2008 | Bachmann |
| 2008/0033501 A1 | 2/2008 | Gross |
| 2008/0046054 A1 | 2/2008 | Hjelle |
| 2008/0051767 A1 | 2/2008 | Rossing |
| 2008/0082137 A1 | 4/2008 | Kieval |
| 2008/0097540 A1 | 4/2008 | Bolea |
| 2008/0140167 A1 | 4/2008 | Hagen |
| 2008/0114439 A1 | 5/2008 | Ramaiah |
| 2008/0132966 A1 | 6/2008 | Levin |
| 2008/0154349 A1 | 6/2008 | Rossing |
| 2008/0161865 A1 | 7/2008 | Hagen |
| 2008/0161887 A1 | 7/2008 | Hagen |
| 2008/0167690 A1 | 7/2008 | Cody |
| 2008/0167693 A1 | 7/2008 | Kieval |
| 2008/0167694 A1 | 7/2008 | Bolea |
| 2008/0167696 A1 | 7/2008 | Cates |
| 2008/0167699 A1 | 7/2008 | Kieval |
| 2008/0171923 A1 | 7/2008 | Bolea |
| 2008/0172101 A1 | 7/2008 | Bolea |

(56) References Cited

U.S. PATENT DOCUMENTS

| | | | |
|---|---|---|---|
| 2008/0172104 | A1 | 7/2008 | Kieval |
| 2008/0177131 | A1 | 7/2008 | Dancu |
| 2008/0181927 | A1 | 7/2008 | Zhao |
| 2008/0194905 | A1 | 8/2008 | Walsh |
| 2008/0195190 | A1 | 8/2008 | Bland et al. |
| 2008/0275539 | A1* | 11/2008 | Williams et al. ............ 623/1.15 |
| 2008/0319504 | A1 | 12/2008 | Loushin |
| 2009/0248138 | A1 | 10/2009 | Golesworthy |
| 2009/0248141 | A1 | 10/2009 | Shandas et al. |
| 2009/0264914 | A1 | 10/2009 | Riina |
| 2009/0292348 | A1 | 11/2009 | Berez et al. |
| 2009/0306756 | A1 | 12/2009 | Cho |
| 2010/0211131 | A1 | 8/2010 | Williams |
| 2011/0077729 | A1 | 3/2011 | Gross et al. |
| 2011/0213408 | A1 | 9/2011 | Gross |
| 2011/0230953 | A1 | 9/2011 | Gross |
| 2011/0230957 | A1 | 9/2011 | Bonsignore et al. |
| 2013/0172981 | A1 | 7/2013 | Gross et al. |
| 2014/0135902 | A1 | 5/2014 | Gross et al. |

FOREIGN PATENT DOCUMENTS

| | | |
|---|---|---|
| EP | 1 153 580 | 11/2001 |
| EP | 1 153 581 | 11/2001 |
| EP | 1 234 554 | 8/2002 |
| EP | 1 343 112 | 9/2003 |
| EP | 1 200 152 | 9/2004 |
| EP | 1 483 730 | 10/2005 |
| WO | WO 01/05463 | 1/2001 |
| WO | WO 01/85063 A1 | 11/2001 |
| WO | WO 02/26314 | 4/2002 |
| WO | WO 03/076008 | 9/2003 |
| WO | WO 03/077191 A1 | 9/2003 |
| WO | WO 03/082080 | 10/2003 |
| WO | WO 03/082403 | 10/2003 |
| WO | WO 2004/073484 | 9/2004 |
| WO | WO 2005/021063 A2 | 3/2005 |
| WO | WO 2005/065771 A1 | 7/2005 |
| WO | WO 2005/084389 | 9/2005 |
| WO | WO 2005/097256 | 10/2005 |
| WO | WO 2005/021063 A3 | 2/2006 |
| WO | WO 2006/012033 | 2/2006 |
| WO | WO 2006/012050 | 2/2006 |
| WO | WO 2006/032902 | 3/2006 |
| WO | WO 2006/040647 | 4/2006 |
| WO | WO 2006/041664 | 4/2006 |
| WO | WO 2006/042280 A2 | 4/2006 |
| WO | WO 2006/125163 | 11/2006 |
| WO | WO 2007/013065 | 2/2007 |
| WO | WO 2007/047152 | 4/2007 |
| WO | WO 2007/080595 | 7/2007 |
| WO | WO 2007/114860 | 10/2007 |
| WO | WO 2007/118090 | 10/2007 |
| WO | WO 2007/136850 | 11/2007 |
| WO | WO 2007/136851 | 11/2007 |
| WO | WO 2008/039982 | 4/2008 |
| WO | WO 2008/083120 | 7/2008 |
| WO | WO 2008/083235 | 7/2008 |
| WO | WO 2009/018394 | 2/2009 |
| WO | WO 2010/035271 | 4/2010 |
| WO | WO 2011/089601 A1 | 7/2011 |

OTHER PUBLICATIONS

An International Search Report dated Feb. 3, 2010, which issued during the prosecution of Applicant's PCT/IL09/00932.

"The effects of altering mean pressure, pulse pressure and pulse frequency on the impulse activity in baroreceptor fibres from the aortic arch and right subclavian artery in the rabbit," Angell James JE, J Physiol. Apr. 1971; 214(1):65-88.

"Theoretical and electrophysiological evidence for axial loading about aortic baroreceptor nerve terminals in rats," Feng B, Am J Physiol Heart Circ Physiol. Dec. 2007; 293(6):H3659-72.

"Ascorbic Acid Selectively Improves Large Elastic Artery Compliance in Postmenopausal Women," Moreau K.L., Hypertension 2005;45: 1107.

"Carotid sinus nerve blockade to reduce blood pressure instability following carotid endarterectomy: a systematic review and meta-analysis," Tang T.Y., Eur J Vasc Endovasc Surg. Sep. 2007; 34(3):304-11, (an abstract).

"Coronary artery baroreceptor-mediated changes in arterial pressure: a pilot study in conscious and anaesthetized sheep," Bennetts J.S., Clin Exp Pharmacol Physiol. Sep. 2001; 28(9):768-72, (an abstract).

"Effect of increased renal venous pressure on renal function," Doty J. M., The Journal of Trauma: Injury, Infection, and Critical Care: Dec. 1999, vol. 47, Issue 6, p. 1000, (an abstract).

"Glomerular ultrafiltration dynamics during increased renal venous pressure," J.R. Dilley, AJP—Renal Physiology, vol. 244, Issue 6 650-F658, (an abstract).

"Implantable penile venous compression device: initial experience in the acute canine model," Paick J., The Journal of Urology 1992, vol. 148, No. 1, pp. 188-191 (an abstract).

S. Levenberg, et al., "Endothelial cells derived from human embryonic stem cells", PNAS Apr. 2, 2002, vol. 99, No. 7 pp. 4391-4396.

B. Ziaie, et al., "An Implantable Pressure Sensor Cuff for Tonometric Blood Pressure Measurement," IEEE Solid-State Sensor and Actuator Workshop, pp. 216-219, Jun. 1998.

Percutaneous Mitral Valve Therapy, Presented by Julie Logan, RN Foundation for Cardiovascular Medicine La Jolla, Jul. 15-17, 2010.

Mendelsohn (1998) Am J Cardiol 82:1077-1081.

Delfino, A., Stergiopulos, N., & Moore, J. E. (1997). Residual Strain Effects on the Stress Field in a Thick Wall Finite Element Model of the Human Carotid Bifurcation. *Science*, 30(8), 777-786.

Mendelowitz, D., & Scher, a M. (1990). Pulsatile pressure can prevent rapid baroreflex resetting. *The American journal of physiology*, 258(1 Pt 2), H92-100. Retrieved from http://www.ncbi.nlm.nih.gov/pubmed/2301618.

Riley, W. A., Barnes, R. W., Evans, G W, Burke, G L, Evans, Gregory W, & Burke, Gregory L. (1992). Ultrasonic measurement of the elastic modulus of the common carotid artery. The Atherosclerosis Risk in Communities (ARIC) Study WA Riley, RW Barnes, GW Evans and GL Burke Stroke 1992;23;952-956 *Stroke*.

"The effect of baroreceptor activity on cardiovascular regulation", by Davos (Hellenic j Cardiol 43: 145-155, 2002).

International search report and written opinion dated Dec. 5, 2012 for PCT/IL2011/000356.

U.S. Appl. No. 13/455,005, filed Apr. 24, 2012, Gross et al.
U.S. Appl. No. 14/092,433, filed Apr. 27, 2013, Gross et al.
Office action dated Jul. 17, 2013 for U.S. Appl. No. 12/602,787.
Office action dated Oct. 31, 2014 for U.S. Appl. No. 12/602,787.
Office action dated Jan. 3, 2013 for U.S. Appl. No. 12/774,254.
Office action dated Jan. 29, 2013 for U.S. Appl. No. 12/602,787.
Office action dated Apr. 19, 2012 for U.S. Appl. No. 12/774,254.
Notice of allowance dated May 7, 2015 for U.S. Appl. No. 12/602,787.
Office action dated Mar. 3, 2015 for U.S. Appl. No. 14/560,194.
Office action dated May 8, 2015 for U.S. Appl. No. No. 13/116,370.
U.S. Appl. No. 14/560,194, filed Dec. 4, 2014, Gross.
U.S. Appl. No. 60/702,491, filed Jul. 25, 2005, Gross.
U.S. Appl. No. 60/721,728, filed Sep. 28, 2005, Gross.
Davos. The effect of baroreceptor activity on cardiovascular regulation. Hellenic J. cardiol. 2002; 43:145-155.
European search report and opinion dated Dec. 14, 2012 for EP Application No. 06766171.
International search report and written opinion dated Jan. 24, 2007 for PCT/IL2006/000856.
Notice of Allowance dated Nov. 20, 2014 for U.S. Appl. No. 11/881,256.
Office action dated Jan. 14, 2013 for U.S. Appl. No. 11/881,256.
Office action dated May 24, 2012 for U.S. Appl. No. 11/881,256.
Office action dated Jun. 23, 2014 for U.S. Appl. No. 11/881,256.
Office action dated Oct. 21, 2014 for U.S. Appl. No. 13/116,370.
Office action dated Nov. 5, 2014 for U.S. Appl. No. 11/881,256.
Office action dated Jan. 2, 2015 for U.S. Appl. No. 13/455,005.

* cited by examiner

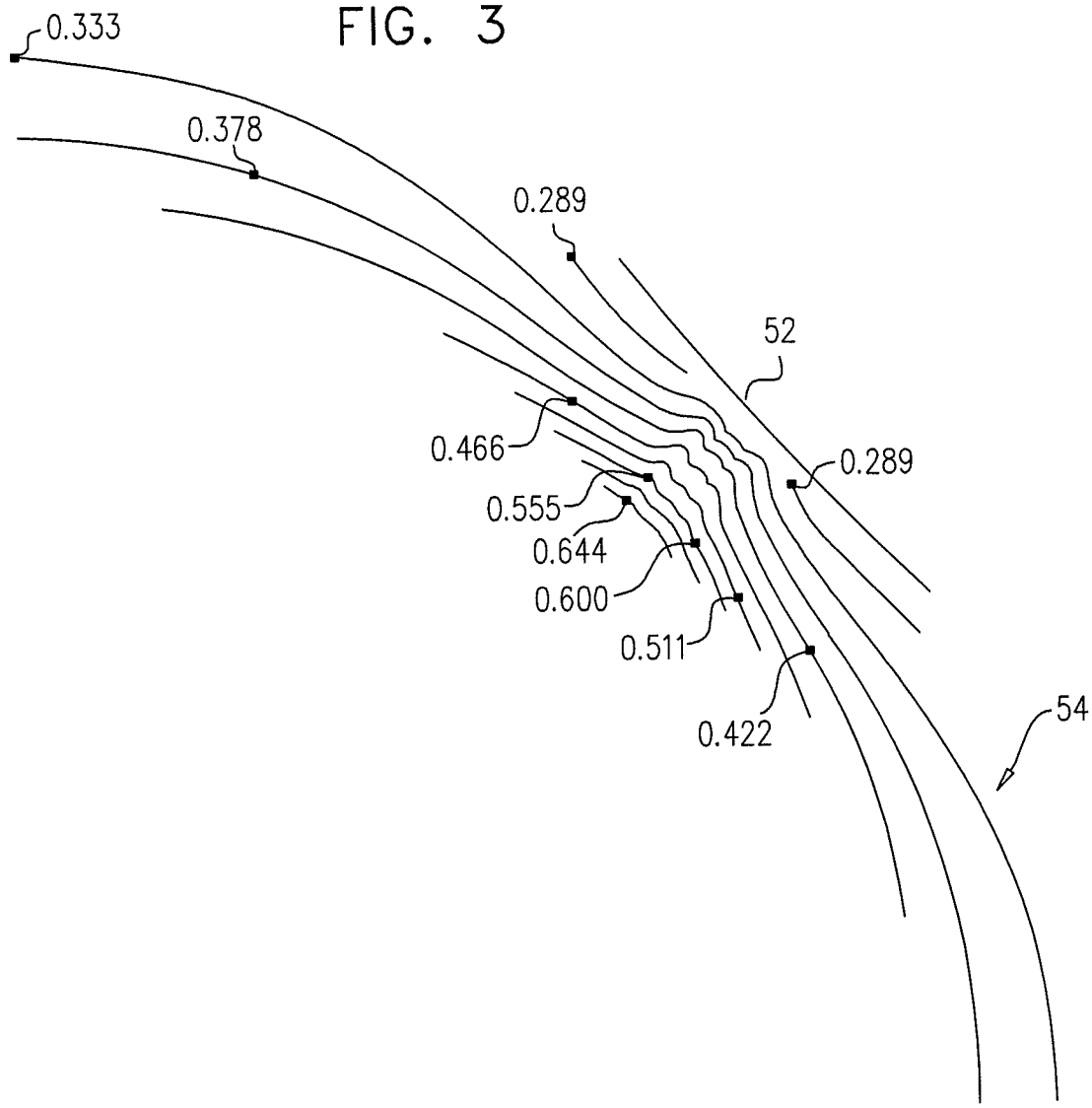

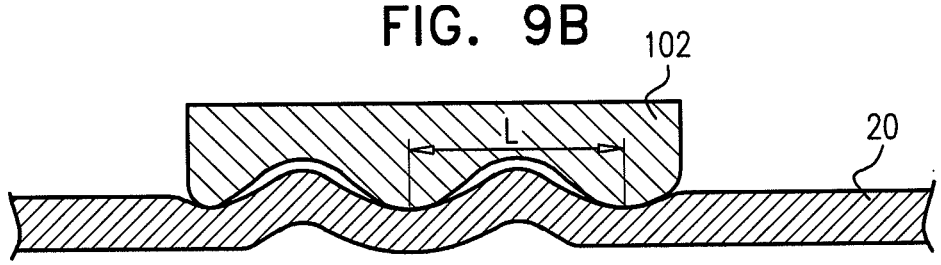
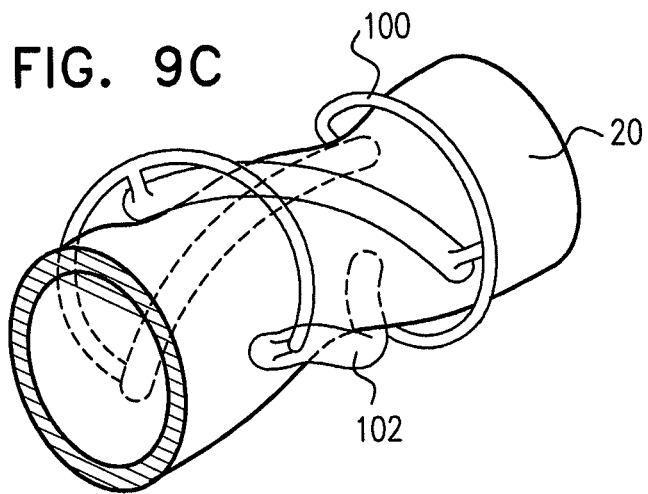
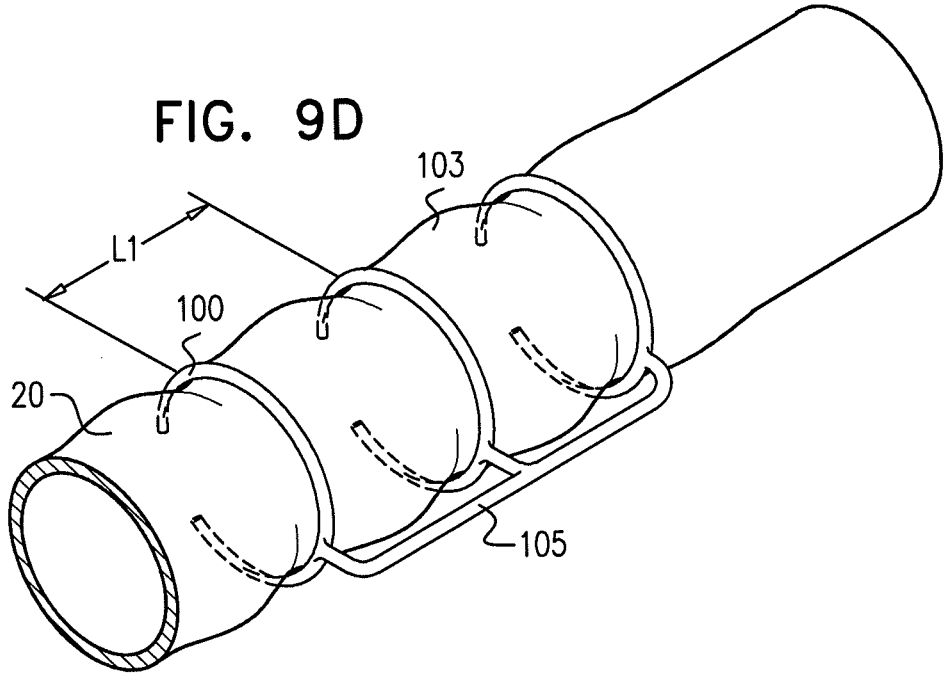

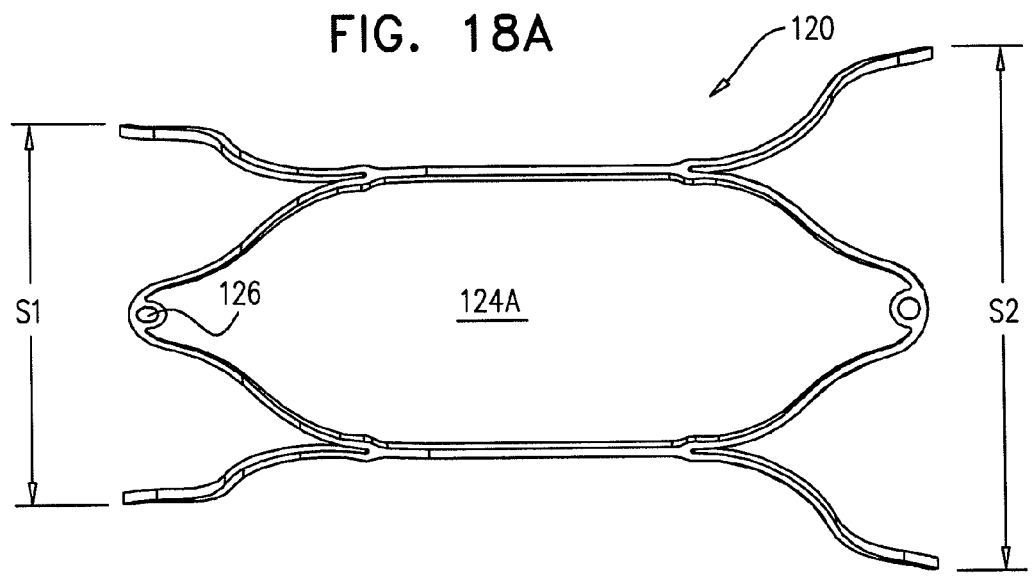
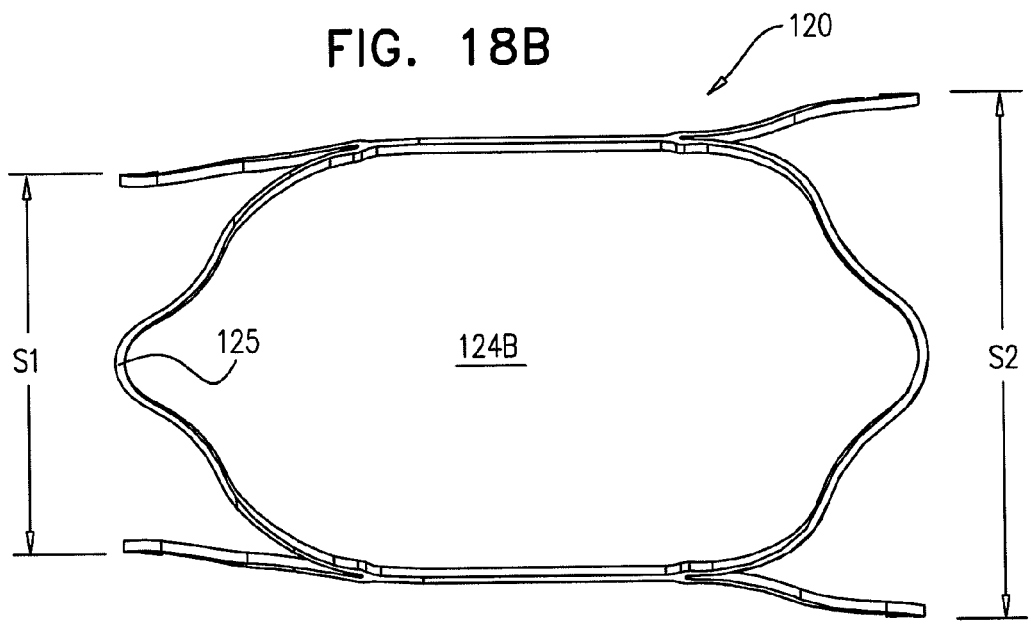

ARB. UNITS ALONG ARC

DEVICES AND METHODS FOR CONTROL OF BLOOD PRESSURE

CROSS-REFERENCES TO RELATED APPLICATIONS

The present patent application is continuation-in-part of U.S. Ser. No. 12/774,254 to Gross et al., filed May 5, 2010, which is a continuation-in-part of U.S. patent application Ser. No. 12/602,787, which is the U.S. national phase of PCT Application No. PCT/IL2009/000932 to Gross et al. (WO 10/035271), filed Sep. 29, 2009, which claims priority from U.S. Patent Application 61/194,339, filed Sep. 26, 2008, entitled "Devices and methods for control of blood pressure."

The present patent application is related to U.S. patent application Ser. No. 11/881,256 (US 2008/0033501), filed Jul. 25, 2007, entitled "Elliptical element for blood pressure reduction," which is a continuation-in-part of PCT Application No. PCT/IL2006/000856 to Gross (WO 07/013065), filed Jul. 25, 2006, entitled, "Electrical stimulation of blood vessels," which claims the benefit of (a) U.S. Provisional Application 60/702,491, filed Jul. 25, 2005, entitled, "Electrical stimulation of blood vessels," and (b) U.S. Provisional Application 60/721,728, filed Sep. 28, 2005, entitled, "Electrical stimulation of blood vessels."

All of the above applications are incorporated herein by reference.

FIELD OF EMBODIMENTS OF THE INVENTION

Some applications of the present invention generally relate to implanted medical apparatus. Specifically, some applications of the present invention relate to apparatus and methods for reducing blood pressure.

BACKGROUND

Hypertension is a condition from which many people suffer. It is a constant state of elevated blood pressure which can be caused by a number of factors, for example, genetics, obesity or diet. Baroreceptors located in the walls of blood vessels act to regulate blood pressure. They do so by sending information to the central nervous system (CNS) regarding the extent to which the blood vessel walls are stretched by the pressure of the blood flowing therethrough. In response to these signals, the CNS adjusts certain parameters so as to maintain a stable blood pressure.

SUMMARY OF EMBODIMENTS

For some applications, a subject's hypertension is treated by modulating the subject's baroreceptor activity. Mechanical and other forces are applied directly or indirectly to one or more of the subject's arteries in order to modulate the baroreceptor response to the blood pressure. The forces are typically applied to arteries that are rich in baroreceptors, for example, the carotid arteries, the aorta, the subclavian arteries and/or arteries of the brain. For some applications, the forces are applied to other regions of the body that contain baroreceptors, such as the atria, the renal arteries, or veins.

Baroreceptors measure strain, which, in the case of a circular vessel, depends on the pressure and the radius of the vessel. As pressure increases, the stress exerted on the wall increases, thereby increasing the strain in the vessel wall. Equation 1 relates the wall stress $\sigma$ in a thin walled tube, to internal pressure p, internal radius r, and wall thickness t.

$$\sigma = pr/2t \qquad \text{[Equation 1]}$$

In a hypertensive patient, the pressure-strain relationship is typically shifted to higher pressures, such that the artery is subject to a given strain at a higher blood pressure than the blood pressure in a healthy vessel that would give rise to the given strain. Thus, the baroreceptors are activated at a higher blood pressure in a hypertensive patient than they are in a healthy patient. The devices described herein typically cause the pressure-strain curve to shift back to lower pressures.

The inventors hypothesize that, at constant pressure, by increasing the radius of curvature of a region of an arterial wall, the strain in the region of the wall may be increased. Thus, the baroreceptor nerve endings in the region (which are typically disposed between the medial and adventitial layers of the artery, as described in further detail hereinbelow) experience greater strain, ceteris paribus. The intravascular devices described herein typically increase the radius of curvature of regions of the arterial wall, but do not cause a substantial decrease in the cross-section of the artery (and, typically, cause an increase in the cross-section of the artery), thereby maintaining blood flow through the artery. For some applications, the devices change the shape of the artery such that the artery is less circular than in the absence of the device, thereby increasing the radius of curvature of sections of the arterial wall.

Typically, the devices described herein change the shape of the artery by being placed inside or outside the artery, but by maintaining less than 360 degrees of contact with the surface of the artery at any given site along the length of the artery. Further typically, contact between the device and the artery is limited to several (e.g., two to six, or three to six) contact regions around the circumference of the artery, and is generally minimized. Still further typically, the device is placed inside the artery such that there are several regions at which the device does not contact the artery, each of the non-contact regions being contiguous, and defining an angle that is greater than 10 degrees around the longitudinal axis of the artery, as described in further detail hereinbelow. This may be beneficial for the following reasons:

(1) A greater area of the artery pulsates in response to pressure changes than if the device were to maintain a greater degree of contact with the vessel wall. It is generally desirable to allow at least a portion of the vessel to pulsate freely. This is because pulsation of the vessel over the course of the cardiac cycle typically activates and maintains normal functioning of the baroreceptors. For some applications, baroreceptor activity in the portions of the vessel that are in contact with the device may be reduced, since the movement of those portions in response to changes in blood pressure is reduced. Therefore, for some applications, contact between the device and the artery is minimized.

(2) A smaller metal to lumen ratio typically causes less reactive growth of endothelial and smooth muscle cells. Typically, reducing this reactive growth reduces the chances of stenosis being caused by the device. Further typically, reducing this reactive growth facilitates explantation, and/or movement of the device, when desired.

For some applications the devices described herein are implanted temporarily, and are subsequently removed. For example, one of the devices described herein may be implanted for a period of less than one month, e.g., less than one week. Temporary implantation of the devices is typically used to treat an acute condition of the subject. For some applications, the shape of the artery in which the device is implanted is permanently altered by temporarily implanting the device.

Typically, the devices described herein are implanted inside or outside of the subject's carotid artery, e.g., at the carotid sinus. In accordance with respective embodiments, the devices are implanted bilaterally, or inside or outside of only one of the subject's carotid arteries. Alternatively or additionally, the devices are placed inside or outside of a different artery, e.g., the aorta or the pulmonary artery.

The devices are typically self-anchoring and structurally stable. Further typically, the devices are passive devices, i.e., subsequent to the devices being implanted inside or outside of the artery, the devices act to increase baroreceptor sensitivity without requiring electrical or real-time mechanical activation.

There is therefore provided, in accordance with some applications of the present invention, a method, including:
  identifying a subject as suffering from hypertension; and
  in response to the identifying,
    (a) increasing a radius of curvature of a first set of at least three regions of an arterial wall of the subject at a given longitudinal location, while
    (b) allowing the first set of regions of the arterial wall to pulsate, by
  implanting a device inside the artery at the longitudinal location such that the device applies pressure to the arterial wall at a second set of at least three regions of the artery, but does not contact the first set of regions, the first set of regions and the second set of regions alternating with each other.

For some applications, implanting the device includes increasing strain in the arterial wall at both the first and the second set of regions, relative to the strain in the arterial wall when the device is absent from the artery.

For some applications, implanting the device includes increasing a cross-sectional area of the artery.

For some applications, implanting the device includes implanting a device such that the second set of regions includes three to six regions at which the device applies pressure to the arterial wall.

For some applications, implanting the device includes implanting the device for less than one month.

For some applications, implanting the device includes implanting the device inside a carotid artery of the subject.

For some applications, implanting the device includes implanting the device inside a pulmonary artery of the subject.

For some applications, implanting the device includes implanting the device inside an aorta of the subject.

For some applications, implanting the device includes placing the device inside the artery and allowing the device to become self-anchored to the artery.

For some applications, implanting the device includes implanting a device having a total cross-sectional area of less than 5 sq mm.

For some applications, implanting the device includes implanting a device having a total cross-sectional area of less than 0.5 sq mm.

For some applications, increasing the radius of curvature of the first set of at least three regions of the arterial wall includes increasing a systolic radius of curvature at the regions to more than 1.1 times the systolic radius of curvature of the arterial wall when the device is absent from the artery.

For some applications, increasing the radius the curvature of the first set of at least three regions of the arterial wall includes increasing a systolic radius of curvature at the regions to more than two times the systolic radius of curvature of the arterial wall when the device is absent from the artery.

For some applications, increasing the radius the curvature of the first set of at least three regions of the arterial wall includes increasing a systolic radius of curvature at the regions to more than twenty times the systolic radius of curvature of the arterial wall when the device is absent from the artery.

For some applications, implanting the device includes implanting the device such that each of the regions of the first set of regions is a contiguous region that is able to pulsate, each of the contiguous regions encompassing an angle around a longitudinal axis of the artery of greater than 10 degrees.

For some applications, implanting the device includes implanting the device such that each of the regions of the first set of regions is a contiguous region that is able to pulsate, each of the contiguous regions encompassing an angle around the longitudinal axis of the artery of greater than 20 degrees.

For some applications, implanting the device includes implanting the device such that each of the regions of the first set of regions is a contiguous region that is able to pulsate, each of the contiguous regions encompassing an angle around the longitudinal axis of the artery of greater than 50 degrees.

For some applications, implanting the device includes implanting the device such that the first set of regions encompass more than 20 percent of a circumference of the arterial wall at the longitudinal location, during systole of the subject.

For some applications, implanting the device includes implanting the device such that the first set of regions encompass more than 80 percent of the circumference of the arterial wall at the longitudinal location, during systole of the subject.

There is further provided, in accordance with some applications of the present invention, apparatus for treating hypertension of a subject, including:
  an implantable device shaped to define at least three separate artery-contacting surfaces, and configured to:
    (a) increase a radius of curvature of a wall of the artery at a first set of at least three regions of the arterial wall at a given longitudinal location, while
    (b) allowing the first set of regions of the arterial wall to pulsate at the longitudinal location, by
  the device being implanted inside the artery at the longitudinal location such that the artery-contacting surfaces contact a second set of at least three regions of the arterial wall, but do not contact the first set of regions of the arterial wall, the first set of regions and the second set of regions alternating with each other.

For some applications, the device is configured such that as the artery-contacting surfaces apply increasing pressure to the arterial wall, a cross-sectional area of the artery increases.

For some applications, the device is configured to increase strain in the arterial wall at both the first and the second set of regions, relative to the strain in the arterial wall when the device is absent from the artery.

For some applications, the device is configured to increase a cross-sectional area of the artery.

For some applications, the artery-contacting surfaces includes three to six artery contacting surfaces.

For some applications, the device is configured to be implanted inside the artery for less than one month.

For some applications, the device is configured to be implanted inside a carotid artery of the subject.

For some applications, the device is configured to be implanted inside a pulmonary artery of the subject.

For some applications, the device is configured to be implanted inside an aorta of the subject.

For some applications, the device is configured to become self-anchored to the artery.

For some applications, the device has a total cross-sectional area of less than 5 sq mm.

For some applications, the device has a total cross-sectional area of less than 0.5 sq mm.

For some applications, edges of at least two adjacent artery-contacting surfaces define an angle around a longitudinal axis of the device of greater than 10 degrees.

For some applications, the edges of the two artery-contacting surfaces define an angle around the longitudinal axis of the device of greater than 20 degrees.

For some applications, the edges of the two artery-contacting surfaces define an angle around the longitudinal axis of the device of greater than 50 degrees.

There is additionally provided, in accordance with some applications of the present invention, a method, including:
 identifying a subject as suffering from hypertension; and
 in response to the identifying,
  (a) increasing strain at a first set of regions of an arterial wall of the subject at a given longitudinal location,
  (b) while maintaining, at a given stage in a cardiac cycle of the subject, a cross-section of the artery at the longitudinal location that is at least 20 percent of the cross-section of the artery at the longitudinal location, at the given stage of the cardiac cycle, when the device is absent, by
 implanting a device outside the artery at the longitudinal location such that the device applies pressure to the arterial wall at the first set of regions of the arterial wall, but does not contact the arterial wall at at least a second set of regions of the arterial wall at the longitudinal location, the first set of regions and the second set of regions alternating with each other.

For some applications, implanting the device includes implanting the device outside a carotid artery of the subject.

For some applications, implanting the device includes implanting the device outside a pulmonary artery of the subject.

For some applications, implanting the device includes implanting the device outside an aorta of the subject.

For some applications, maintaining the cross-section of the artery that is at least 20 percent of the cross-section of the artery at the longitudinal location when the device is absent, includes maintaining an internal diameter of the artery, in the presence of the device, that is at least 30 percent of the diameter of the artery in the absence of the device.

For some applications, maintaining the cross-section of the artery that is at least 20 percent of the cross-section of the artery at the longitudinal location when the device is absent, includes maintaining a rate of blood flow through the artery that is more than 70 percent of the rate of blood flow through the artery in the absence of the device.

For some applications, maintaining the rate of blood flow through the artery that is more than 70 percent of the rate of blood flow through the artery in the absence of the device, includes maintaining a rate of blood flow through the artery that is more than 90 percent of the rate of blood flow through the artery in the absence of the device.

For some applications, implanting the device includes implanting the device such that the arterial wall is able to pulsate at each of the second set of regions.

For some applications, implanting the device includes implanting a device outside the artery at the longitudinal location such that the device applies pressure to the arterial wall at a first set of three to six regions of the artery, but does not contact the artery at a second set of three to six regions of the artery.

For some applications, implanting the device includes implanting a device outside the artery at the longitudinal location such that the device does not contact the artery at at least the second set of regions of the artery, each of the second set of regions being contiguous, and encompassing an angle around a longitudinal axis of the artery of greater than 10 degrees.

For some applications, implanting the device includes implanting a device such that each of the second set of regions encompasses an angle around the longitudinal axis of the artery of greater than 20 degrees.

For some applications, implanting the device includes implanting a device such that each of the second set of regions encompasses an angle around the longitudinal axis of the artery of greater than 50 degrees.

For some applications, implanting the device includes implanting the device such that the device encompasses less than 90 percent of a circumference of the artery.

For some applications, implanting the device includes implanting the device such that the device encompasses less than 70 percent of the circumference of the artery.

There is additionally provided, in accordance with some applications of the present invention, apparatus for treating hypertension of a subject, including:
 an implantable device shaped to define a single pair of artery-contacting surfaces, and configured to:
  (a) increase a radius of curvature of the artery at a first set of two regions of the artery at a given longitudinal location, while
  (b) allowing the first set of regions of the artery to pulsate at the longitudinal location, by
 the device being implanted inside the artery at the longitudinal location such that the artery-contacting surfaces contact a second set of two regions of the artery, but at no point during a cardiac cycle of the subject does the device contact the first set of regions, the first set of regions and the second set of regions alternating with each other.

For some applications, the device is configured such that when the device is implanted in the artery no portion of the device intersects a longitudinal axis of the artery.

For some applications, the device further includes a joint configured to couple the artery-contacting surfaces to one another, and the joint is disposed asymmetrically with respect to centers of the artery-contacting surfaces.

There is further provided, in accordance with some applications of the present invention, apparatus configured to be implanted into an artery of a subject via a catheter, the apparatus including:
 an implantable device shaped to define:
  at least two artery-contact regions, the artery-contact regions including struts that are configured to stretch an arterial wall by applying pressure to the arterial wall, and
  at least two crimping regions that include locking mechanisms configured to prevent the crimping regions from becoming crimped due to pressure from the wall of the artery on the artery-contact regions,
  the crimping regions being configured to be crimped during insertion of the device, via the catheter, by the locking mechanisms being unlocked during insertion of the device via the catheter.

For some applications, the crimping region defines two struts that are disposed adjacently to one another, and the locking mechanism includes an interface between the two struts that locks the struts with respect to one another.

For some applications, an end of at least one of the artery-contact regions defines a crimping arch, the artery-contact region being configured to be crimped about the crimping arch, the crimping arch having a radius of curvature of less than 0.6 mm.

For some applications, the end of the artery contact-region defines a crimping arch having a radius of curvature of more than 0.3 mm.

For some applications, the struts of the artery-contact regions project outwardly from the crimping arch at an angle that is greater than 30 degrees.

For some applications, the struts of the artery-contact regions project outwardly from the crimping arch at an angle that is greater than 60 degrees.

For some applications, the struts of the artery-contact regions project outwardly from the crimping arch at an angle that is greater than 75 degrees.

For some applications, a maximum span of the device increases along a direction of a longitudinal axis of the device from a first end of the device to a second end of the device.

For some applications, the second end of the device is configured to be placed in a carotid sinus of the subject, and the first end of the device is configured to be placed in an internal carotid artery of the subject.

For some applications, a ratio of the maximum span of the device at the second end of the device to the maximum span of the device at the first end of the device is between 1.1:1 and 2:1.

For some applications, a ratio of the maximum span of the device at the second end of the device to the maximum span of the device at the first end of the device is between 1.1:1 and 1.4:1.

For some applications, the artery-contacting regions each include two or more struts that are longitudinally translated with respect to one another.

For some applications, the apparatus further includes a reinforcing element configured to couple the two or more struts to one another, and to maintain the longitudinal translation of the struts with respect to one another when the device is crimped.

For some applications, the device has a total cross-sectional area of less than 5 sq mm.

For some applications, the device has a total cross-sectional area of less than 0.5 sq mm.

There is additionally provided, in accordance with some applications of the present invention, apparatus, including:
 an implantable device shaped to define at least two separate artery-contacting strut portions that diverge from each other, from a first end of the device to a second end of the device, and configured:
  to cause a cross-sectional area of a portion of the artery to increase from the first end of the portion to the second end of the portion, while allowing a set of regions of the arterial wall of the portion that are between the struts to pulsate,
  by the device being implanted inside the artery between the first and second ends of the portion.

For some applications, at least one end of the device defines a crimping arch, the device being configured to be crimped about the crimping arch, the crimping arch having a radius of curvature of less than 0.6 mm.

For some applications, the end of the device defines a crimping arch having a radius of curvature of more than 0.3 mm.

For some applications, struts of the strut portions project outwardly from the crimping arch at an angle that is greater than 30 degrees.

For some applications, the struts of the strut portions project outwardly from the crimping arch at an angle that is greater than 60 degrees.

For some applications, the struts of the strut portions project outwardly from the crimping arch at an angle that is greater than 75 degrees.

For some applications, a maximum span of the device increases along a direction of a longitudinal axis of the device from a first end of the device to a second end of the device.

For some applications, the second end of the device is configured to be placed in a carotid sinus of the subject, and the first end of the device is configured to be placed in an internal carotid artery of the subject.

For some applications, a ratio of the maximum span of the device at the second end of the device to the maximum span of the device at the first end of the device is between 1.1:1 and 2:1.

For some applications, a ratio of the maximum span of the device at the second end of the device to the maximum span of the device at the first end of the device is between 1.1:1 and 1.4:1.

For some applications, the strut portions each include two or more struts that are longitudinally translated with respect to one another.

For some applications, the apparatus further includes a reinforcing element configured to couple the two or more struts to one another, and to maintain the longitudinal translation of the struts with respect to one another when the device is crimped.

For some applications, the device has a total cross-sectional area of less than 5 sq mm.

For some applications, the device has a total cross-sectional area of less than 0.5 sq mm.

There is further provided, in accordance with some applications of the present invention, apparatus, including:
 an implantable device shaped to define at least four artery-contacting strut portions that are parallel to each other, each of the strut portions being disposed at a first distance from a first adjacent strut portion, and at a second distance from a second adjacent strut portion, the second distance being greater than the first distance.

For some applications, the at least four artery-contacting strut portions include exactly four artery-contacting strut portions.

For some applications, a ratio of the second distance to the first distance is between 1.1:1 and 5:1.

For some applications, the ratio of the second distance to the first distance is between 1.5:1 and 3:1.

For some applications, the device has a total cross-sectional area of less than 5 sq mm.

For some applications, the device has a total cross-sectional area of less than 0.5 sq mm.

For some applications, at least one end of the device defines a crimping arch, the device being configured to be crimped about the crimping arch, the crimping arch having a radius of curvature of less than 0.6 mm.

For some applications, the end of the device defines a crimping arch having a radius of curvature of more than 0.3 mm.

For some applications, struts of the strut portions project outwardly from the crimping arch at an angle that is greater than 30 degrees.

For some applications, the struts of the strut portions project outwardly from the crimping arch at an angle that is greater than 60 degrees.

For some applications, the struts of the strut portions project outwardly from the crimping arch at an angle that is greater than 75 degrees.

There is further provided, in accordance with some applications of the present invention, a method, including:
  inserting into an artery of a subject, via a catheter, an implantable device that is shaped to define:
    at least two artery-contact regions, the artery-contact regions including struts, and
    at least two crimping regions that include locking mechanisms configured to prevent the crimping regions from becoming crimped due to pressure from the wall of the artery on the artery-contact regions,
    the insertion being performed by crimping the crimping regions during insertion of the device, by unlocking the locking mechanism during insertion of the device via the catheter;
  advancing the device out of a distal end of the catheter; and
  upon advancing the device out of the distal end of the catheter, stretching a wall of the artery by applying pressure to the arterial wall with the struts, by locking the locking mechanism.

There is additionally provided, in accordance with some applications of the present invention, a method, including:
  identifying a subject as suffering from hypertension; and
  in response thereto:
    causing a cross-sectional area of a portion of an artery of the subject to increase from the first end of the portion to the second end of the portion, while allowing a set of regions of the arterial wall of the portion to pulsate, by implanting inside the artery, between the first and second ends of the portion, an implantable device shaped to define at least two separate artery-contacting strut portions that diverge from each other, from a first end of the device to a second end of the device.

There is additionally provided, in accordance with some applications of the present invention, a method for treating hypertension in a patient, said method including:
  selecting a patient diagnosed with hypertension; and
  implanting a device proximate a baroreceptor in a blood vessel wall of the patient proximate the baroreceptor, the blood vessel having a generally cylindrical circumference prior to implanting the device, the implanting of the device flattening one or more regions about the circumference to reduce systemic blood pressure.

For some applications, the device is implanted in an artery selected from the group consisting of a renal artery, the aorta, a subclavian artery, a carotid artery, and an artery of the brain.

For some applications, 3 to 6 regions are flattened.
For some applications, 3 to 4 regions are flattened.
For some applications, 3 regions are flattened.
For some applications, 4 regions are flattened.
For some applications, the flattened regions have substantially equal widths in the circumferential direction.
For some applications, at least some of the flattened regions have different widths in the circumferential direction than do others of the circumferential portions.
For some applications, the device flattens regions that extend along a length of the blood vessel wall in the range from 10 mm to 30 mm.

There is additionally provided, in accordance with some applications of the present invention, a self-expanding stent consisting of from three to six elongate struts, each strut having a proximal end and a distal end, said struts being expandably coupled to each other at their proximal and distal ends but otherwise being free from structure therebetween along their lengths.

For some applications, the struts are arranged axially.
For some applications, the struts are arranged helically.
For some applications, adjacent struts are equally spaced-apart from each other.
For some applications, not all adjacent struts are equally spaced-apart.
For some applications, the struts have a length of at least 10 mm between their proximal and distal ends.

The present invention will be more fully understood from the following detailed description of embodiments thereof, taken together with the drawings, in which:

BRIEF DESCRIPTION OF THE DRAWINGS

FIG. 3 is a contour plot of the strain in the wall of an artery, an extravascular device having been implanted outside the wall, in accordance with some applications of the present invention;

FIGS. 9A-D are schematic illustrations of extravascular devices placed around an artery, in accordance with some applications of the present invention;

FIGS. 18A-D are schematic illustrations of further devices for placing in a subject's artery, in accordance with some applications of the present invention;

DETAILED DESCRIPTION OF EMBODIMENTS

Figure 1:
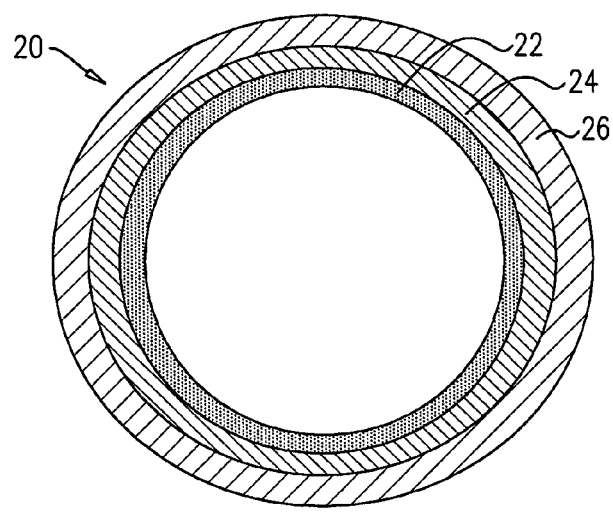
FIG. 1 is a cross-sectional illustration of an artery.

Reference is now made to FIG. 1, which is a cross-sectional illustration of an artery 20. The arterial wall includes three layers 22, 24, and 26, which are called, respectively, the intima, the media, and the adventitia. For some applications of the present invention, an intravascular device is placed inside an artery, baroreceptors being disposed at the interface between adventitia 26 and media 24 of the artery. The device causes the curvature of the arterial wall to flatten in some regions of the circumference of the arterial wall, thereby causing the baroreceptors to become stretched, while allowing the regions to pulsate over the course of the subject's cardiac cycle.

Figure 2A:
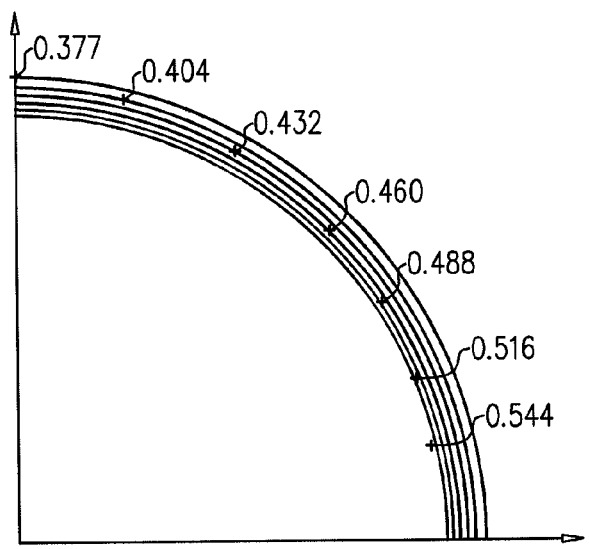
FIGS. 2A-B are contour plots of the strain in the wall of an artery, respectively, when the artery does have and does not have inserted therein an intravascular device, in accordance with some applications of the present invention.
Figure 2B:
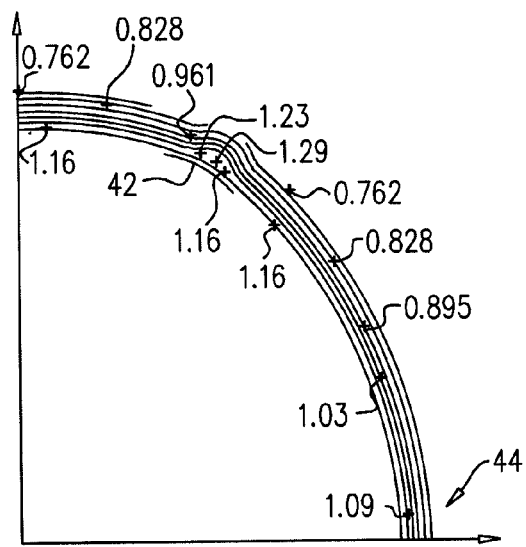

Reference is now made to FIGS. 2A and 2B, which are contour plots of the strain in the top right quarter of an arterial wall, in the absence of an intravascular device (FIG. 2A) and in the presence of an intravascular device (FIG. 2B), analyzed and/or provided in accordance with some applications of the present invention. The contour plot in FIG. 2B was generated for a device (e.g., as shown hereinbelow in FIGS. 7A-B) having four elements, each of which contacts the arterial wall at a contact region 42. The contour plots shown in FIGS. 2A-B are computer simulations of the strain in the wall of an artery, at a blood pressure of 100 mmHg, the artery having a radius of 3 mm, and a wall thickness of 0.6 mm. The scope of the present application includes intravascular devices having different structures from that used to generate FIG. 2B, as would be obvious to one skilled in the art.

As seen in FIGS. 2A-B, relative to the strain in the arterial wall in the absence of an intravascular device, the intravascular device causes there to be increased strain in the arterial wall both (a) in the vicinity of contact regions 42, at which the arterial wall becomes more curved than in the absence of the device, and (b) in flattened regions 44 of the wall, in which regions the arterial wall is flatter than it is in the absence of the device. Thus, the intravascular device increases the strain in the arterial wall even in regions of the arterial wall which are able to pulsate, i.e., flattened regions 44. The increased strain in the flattened regions relative to the strain in the wall in the absence of the intravascular device is due to the increased radius of curvature of the flattened regions of the wall.

Reference is now made to FIG. 3, which is a contour plot of the strain in the top right quarter of an arterial wall, in the presence of an extravascular device, in accordance with some applications of the present invention. The contour plot in FIG. 3 was generated for a device having four elements that contact the artery at four contact regions 52. However, the scope of the present invention includes extravascular devices having different structures, as described hereinbelow. For example, an extravascular device may provide three to six contact regions. The contour plot shown in FIG. 3 is a computer simulation of the strain in the wall of an artery, at a blood pressure of 100 mmHg, the artery having a radius of 3 mm, and a wall thickness of 0.6 mm.

As may be observed by comparing FIG. 3 to FIG. 2A, the extravascular device causes there to be strain in the arterial wall in the vicinity of contact regions 52, at which the arterial wall becomes more curved than in the absence of the device. Furthermore, it may be observed that the strain at non-contact regions 54 of the wall is lower than in the absence of the device. The extravascular device typically breaks the circumferential symmetry of the arterial strain by applying force at discrete points or surfaces around the sinus. For some applications, the extravascular device increases the strain in certain regions of the arterial wall, and decreases the strain in other regions of the arterial wall, while maintaining the average strain almost unchanged or even slightly reduced with respect to the strain in the wall in the absence of the device. For some applications, the extravascular device increases the strain in the arterial wall even at non-contact regions 54, by causing the non-contact regions to become more curved than in the absence of the device.

Figure 4:
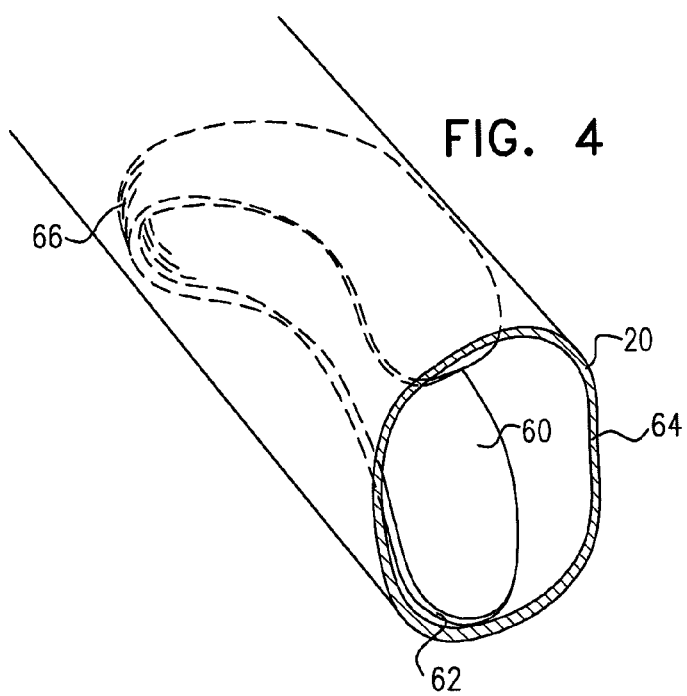
FIG. 4 is a schematic illustration of an intravascular device for placing inside an artery of a subject suffering from hypertension, in accordance with some applications of the present invention.

Reference is now made to FIG. 4, which is a schematic illustration of an intravascular device 60 for placing inside artery 20 of a subject suffering from hypertension, in accordance with some applications of the present invention. As shown, device 60 contacts the arterial wall at two contact regions 62. At the contact regions, device 60 pushes the arterial wall outward, thereby flattening non-contact regions 64 of the arterial wall between the contact regions. Typically, non-contact regions 64 are flattened, or partially flattened during diastole of the subject, but expand during systole such that they become more curved than during diastole. Therefore, strain in the flattened regions of the arterial wall is increased. However, the flattened regions still pulsate over the course of the subject's cardiac cycle in the presence of device 60.

As shown, device 60 is shaped such that the device substantially does not reduce blood flow. Typically, device 60 is shaped such that no portion of the device intersects the longitudinal axis of the artery. For example, as shown, contact surfaces of the device (which contact the arterial wall at contact regions 60) are coupled to each other by a joint 66 that does not intersect the longitudinal axis of the artery. The joint is disposed asymmetrically with respect to centers of the contact surfaces of the device.

Figure 5A:
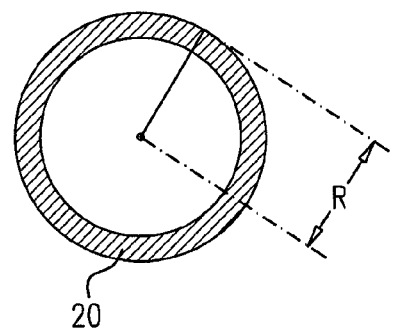
FIGS. 5A-B are schematic illustrations of an artery, showing the radius of curvature of the artery, respectively, before and after placement of the device shown in FIG. 4, in accordance with some applications of the present invention.
Figure 5B:
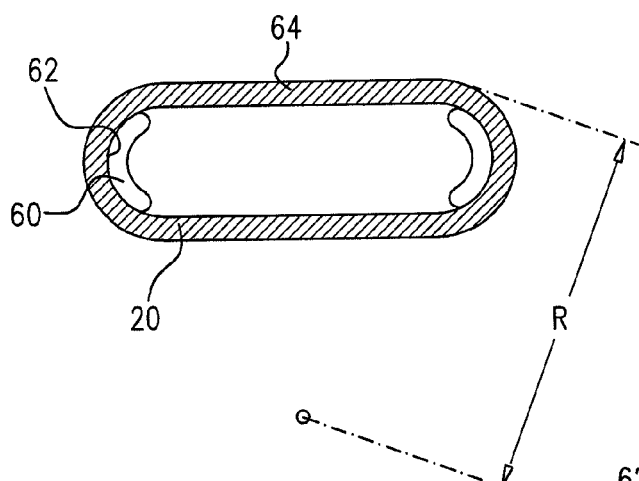

Reference is now made to FIGS. 5A-B, which are schematic illustrations of an artery, showing the radius R of artery 20, respectively, before and after placement of the device 60 shown in FIG. 4, in accordance with some applications of the present invention. It may be observed that, for some applications, insertion of device 60 increases the systolic radius of curvature of the artery at non-contact regions 64, for example, such that the radius of curvature at non-contact regions 64 is more than 1.1 times (e.g., twice, or more than twenty times) the systolic radius of curvature of regions 64 in the absence of device 60, ceteris paribus. For some applications, device 60 causes the radius of curvature of at least a portion of a non-contact region to become infinite, by flattening the non-contact regions. For example, the center of non-contact region 64 in FIG. 5B has an infinite radius of curvature.

For some applications, device 60 increases the systolic radius of curvature of the artery at non-contact regions 64 in the aforementioned manner, and increases the systolic cross-sectional area of the artery by more than five percent (e.g., ten percent), relative to the systolic cross-sectional area of the artery in the absence of device 60.

In accordance with the description hereinabove, by flattening non-contact regions 64 of the wall of artery 20, device 60 causes increased strain in regions 64, thereby causing an increase in baroreceptor firing at regions 64. Alternatively or additionally, device 60 causes increased baroreceptor firing at contact regions 62, by deforming the arterial wall at the contact regions.

Typically, device 60 exerts a force on artery 20, such that, during systole when the artery is in the stretched configuration shown in FIG. 5B, non-contact regions 64 comprise more than ten percent, e.g., more than 20 percent, of the circumference of the arterial wall at longitudinal sites at which device 60 stretches the artery. For some applications, during systole, non-contact regions 64 comprise more than 60 percent, e.g., more than 80 percent, of the circumference of the arterial wall at longitudinal sites at which device 60 stretches the artery.

Figure 5C:
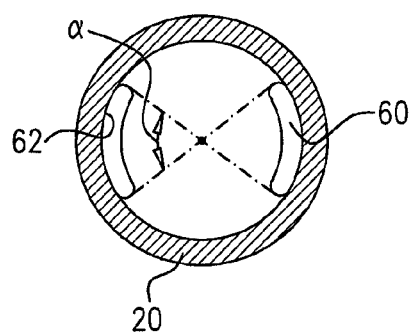
FIG. 5C is a schematic illustration of the device of FIG. 4 disposed inside the artery, without stretching the artery, for illustrative purposes.

Reference is now made to FIG. 5C, which shows device 60 disposed inside artery 20, but without the device stretching artery 20. FIG. 5C is for illustrative purposes, since typically once device 60 is inserted into the artery, the device will stretch the artery, as shown in FIG. 5B. FIG. 5C demonstrates that the device contacts the walls of the artery at contact regions 62 at less than 360 degrees of the circumference of the artery at any longitudinal point along artery 20 (e.g., at the cross-section shown in FIGS. 5A-C). As shown in FIG. 5C, each of the contact regions 62 encompasses an angle alpha of the circumference of the artery, such that the contact that device 60 makes with the walls of the artery encompasses two times alpha degrees. For devices that contact the artery at more than two contact regions, the contact that the device makes with the walls of the artery encompasses an angle that is a correspondingly greater multiple of alpha degrees. Typically, device 60 (and the other intravascular devices described herein) contacts the walls of the artery at less than 180 degrees (e.g., less than 90 degrees) of the circumference of the artery at any longitudinal site along the artery. Typically, device 60 contacts the walls of the artery at more than 5 degrees (e.g., more than 10 degrees) of the circumference of the artery at any longitudinal site along the artery. For example, device 60 may contact the walls of the artery at 5-180 degrees, e.g., 10-90 degrees, at a given longitudinal site.

Figure 6A:
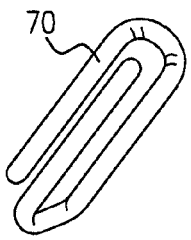
FIGS. 6A-B are schematic illustrations of, respectively, a device, and the device implanted inside an artery, in accordance with some applications of the present invention.
Figure 6B:
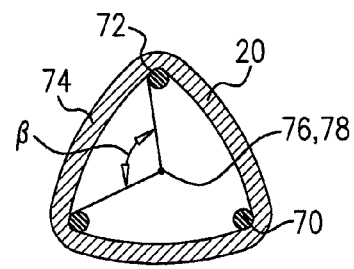

Reference is now made to FIGS. 6A-B, which are schematic illustrations of, respectively, a device 70, and device 70 implanted inside artery 20, in accordance with some applications of the present invention. Device 70 contacts the wall of the artery at three contact regions 72, thereby increasing the radius of curvature (i.e., flattening) of non-contact regions 74 of the artery that are between the contact regions. The flattened non-contact regions and the contact regions alternate with each other. The flattened non-contact regions are typically able to pulsate over the course of the subject's cardiac cycle, as described hereinabove. As shown in FIG. 6B, each contiguous non-contact region at a given longitudinal site of the artery, encompasses an angle beta around a longitudinal axis 76 of the artery. For some devices (e.g., device 70, and device 90 described hereinbelow with reference to FIGS. 8A-B), the angle beta is also defined by the angle that edges of adjacent contact regions of the device define around longitudinal axis 78 of the device. When the device is placed in the artery longitudinal axis 78 of the device is typically aligned with longitudinal axis 76 of the artery. Typically, angle beta is greater than 10 degree, e.g., greater than 20 degree, or greater than 50 degrees. Further typically, angle beta is less than 180 degrees, e.g., less than 90 degrees. For some applications angle beta is 10-180 degree, e.g., 20-90 degrees. Typically, each of the contiguous non-contact regions is able to pulsate.

Figure 7A:
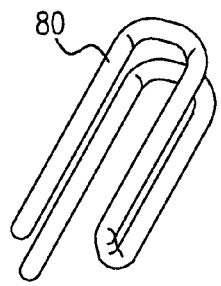
FIGS. 7A-B are schematic illustrations of, respectively, another device, and the device implanted inside an artery, in accordance with some applications of the present invention.
Figure 7B:
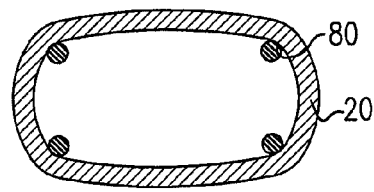

Reference is now made to FIGS. 7A-B, which are schematic illustrations of, respectively, a device 80, and device 80 implanted inside artery 20, in accordance with some applications of the present invention. Device 80 contacts the wall of the artery at four contact regions, thereby flattening the non-contact regions of the artery that are between the contact regions. Each contiguous non-contact region at a given longitudinal site of the artery, encompasses an angle beta around the longitudinal axis of the artery, angle beta being as described hereinabove.

Figure 8A:
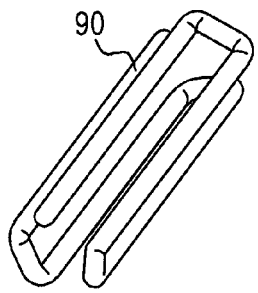
FIGS. 8A-B are schematic illustrations of, respectively, a further device, and the device implanted inside an artery, in accordance with some applications of the present invention.
Figure 8B:
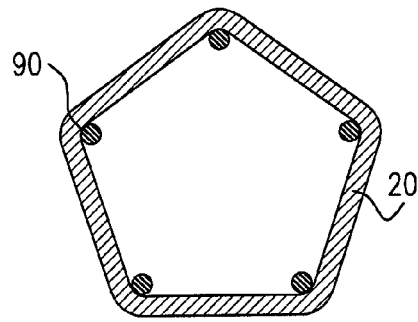

Reference is now made to FIGS. 8A-B, which are schematic illustrations of, respectively, a device 90, and device 90 implanted inside artery 20, in accordance with some applications of the present invention. Device 90 contacts the wall of the artery at five contact regions, thereby flattening the non-contact regions of the artery that are between the contact regions. Each contiguous non-contact region at a given longitudinal site of the artery, encompasses an angle beta around the longitudinal axis of, angle beta being as described hereinabove.

Apart from the fact that devices 70, 80, and 90 contact the artery at, respectively three, four, and five contact regions, devices 70, 80, and 90 function in a generally similar manner to each other, and to device 60, described with reference to FIGS. 4 and 5A-C. For example, devices 70, 80, and 90 typically contact the arterial wall around substantially less than 360 degrees of the circumference of the artery, for example, around 10-90 degrees, or around an angle as described hereinabove with reference to FIGS. 5A-C. Furthermore, devices 70, 80, and 90 typically increase the cross-sectional area of the artery relative to the cross-sectional area of the artery in the absence of the device.

For some applications, a device having three or more contact regions with the arterial wall, for example, as shown in FIGS. 6A-8B, is used. It is noted that since device 60 (shown in FIG. 4) contacts the artery at two contact points, as the device applies increasing pressure to the artery, it will, at a given stage, decrease the cross-section of the artery, as the artery becomes increasingly elliptical. By contrast, devices 70, 80, and 90, which contact the artery at three or more contact points, increase the cross-section of the artery, as they apply increasing pressure to the wall of the artery. Thus, for some applications, a device with three or more contact regions is used in order that the cross-sectional area of the artery is increased as the force which the device exerts on the wall increases, as compared with a device with only two contact regions.

Although devices that contact artery 20 at two, three, four and five contact regions have been described, the scope of the present invention includes devices that contact the artery at a different number of contact regions, and/or that have different structures from those shown, mutatis mutandis.

The intravascular devices described herein are generally shaped such that the devices contact the intravascular wall at relatively small contact regions, and provide relatively large contiguous non-contact regions, which are able to pulsate due to the subject's cardiac cycle.

The devices are typically shaped such that the total contact region that the device makes with the arterial wall at any longitudinal point along the artery is less than 2 mm, e.g., less than 0.5 mm. The contact region is usually larger than 0.05 mm, e.g., greater than 0.2 mm. For example, the contact region may be 0.05-2 mm, e.g., 0.1-0.4 mm, or 0.2-0.5 mm. The devices are typically inserted into an artery that has an internal circumference during systole of 6-8 mm. Thus, the intravascular devices described herein are typically configured to contact less than 35 percent of the circumference of the artery at any longitudinal point along the artery, and at any point in the subject's cardiac cycle (or, for at least a portion of the cardiac cycle). Further typically, the intravascular devices described herein are configured to contact more than 0.5 percent of the circumference of the artery at any longitudinal point along the artery, and at any point in the subject's cardiac cycle (or, for at least a portion of the cardiac cycle). For some applications, the contact region may be 0.5-35 percent of the circumference of the artery (or, for at least a portion of the cardiac cycle).

For some applications, the intravascular devices described herein have a total cross-sectional area of less than 5 sq mm, e.g., less than 0.8 sq mm, or less than 0.5 sq mm. (The total cross-sectional area should be understood to refer to the cross-sectional area of the solid portions of the devices, and not the space in between the solid portions.) The devices typically have this cross-sectional area over a length of the device of more than 4 mm, e.g., more than 6 mm, and/or less than 12 mm, e.g. less than 10 mm. For example, the devices may have the aforementioned cross sectional area over a length of 4 mm-12 mm, e.g., 6 mm-10 mm. The devices are typically manufactured from nitinol, and/or passivated stainless steel 316L.

Figure 9A:
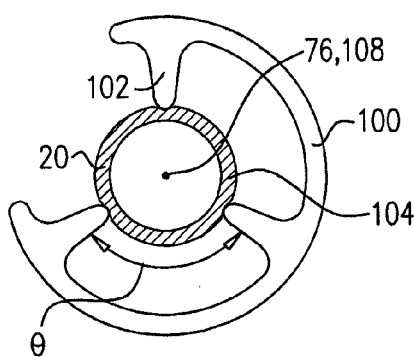

Reference is now made to FIGS. 9A-D, which are schematic illustrations of extravascular devices 100 that are implanted around the outside of artery 20, in accordance with some applications of the present invention. For some applications, an extravascular device having three contact elements 102 (as shown in FIGS. 9A and 9C) is placed around the artery. Alternatively, the extravascular device has a different number of contact elements 102, e.g., four to six contact elements. The contact elements increase the strain in the arterial wall at the regions at which the contact elements contact the arterial wall, relative to the strain in the arterial wall in the absence of device 100. For some applications, the device increases the strain in the arterial wall even at regions of the arterial wall between the contact regions, relative to the strain of the arterial wall in the absence of the device.

As with the intravascular devices described hereinabove, typically contact between extravascular device 100 and the artery at a given longitudinal location is limited to several (e.g., three to six) contact regions around the circumference of the artery, and is generally minimized. Thus, when the device is placed around the artery there is at least one, and typically a plurality of, non-contact regions 104 around the circumference of the artery, at which the device does not contact the arterial wall. As shown in FIG. 9A, each contiguous non-contact region at a given longitudinal site of the artery, encompasses an angle theta around a longitudinal axis 76 of the artery. For some devices, as shown, the angle theta is also defined by the edges of adjacent contact elements 102 of the device and longitudinal axis 108 of the device. When the device is placed in the artery longitudinal axis 108 of the device is typically aligned with longitudinal axis 76 of the artery.

Typically, angle theta is greater than 10 degree, e.g., greater than 20 degree, or greater than 50 degrees. Further typically, angle theta is less than 180 degrees, e.g., less than 90 degrees. For some applications angle theta is 10-180 degree, e.g., 20-90 degrees. This may be beneficial, since providing contiguous non-contact regions around the artery, as described, allows a greater area of the artery to pulsate in response to pressure changes than if the device were to provide smaller contiguous non-contact regions.

FIG. 9E shows a cross-section of one of contact elements 102 on a wall of artery 20, in accordance with some applications of the present invention. For some applications, some or all of contact elements 102 are shaped to define grooves. Each of the grooves has a length L. Typically, length L is more than 0.5 mm (e.g., more than 2 mm), and/or less than 8 mm (e.g., less than 6 mm). For example, length L may be 0.5-8 mm, e.g., 2-6 mm. The contact element typically facilitates pulsation of the arterial wall into the groove.

Typically (as shown for example in FIGS. 9A and 9C), extravascular device 100 does not encompass the full circumference of the artery. For example, the extravascular device may encompass less than 90 percent, e.g., less than 70 percent of the circumference of the artery. For some applications, using a device that does not encompass the whole circumference of the artery facilitates placement of the device on the artery. For example, it may be possible to place such a device on the artery (a) without dissecting the artery free from its surrounding tissues, and/or (b) without fully mobilizing the artery.

For some applications, using a device that does not encompass the whole circumference of the artery reduces damage to the artery, and/or damage to baroreceptors, during placement of the device on the artery. Alternatively or additionally, using a device that does not encompass the whole circumference of the artery makes placement of the device on the artery a less complex procedure than placement on the artery of a device that fully encompasses the artery.

For some applications, device 100 does not encompass the whole circumference of the artery, and contact elements 102 curve around the artery, as shown in FIG. 9C. Typically, the curvature of the contact elements facilitates coupling of device 100 to the artery.

Typically, extravascular device 100 encompasses more than 50 percent of the circumference of the artery, for example, in order to prevent the device from slipping from the artery. However, the scope of the present invention includes devices that encompass less than 50 percent of the artery.

For some applications, extravascular device 100 encompasses the whole circumference of artery 20. For example, an extravascular device may be used that comprises two pieces that are coupled to each other such that the device encompasses the whole artery.

Typically, the device causes an increase in the strain in at least a portion of the arterial wall, relative to the strain in the arterial wall in the absence of the device, without substantially reducing the cross-sectional area of the artery. For example, the cross-sectional area of the artery in the presence of device 100 may be more than 50 percent, e.g., more than 80 percent of the cross-sectional area of the artery in the absence of the device, at a given stage in the subject's cardiac cycle. The device does not cause a substantial reduction in the cross-sectional area of the artery because the device only contacts the artery at discrete points around the circumference of the artery. Therefore the device does not substantially constrict the artery, but rather reshapes the artery relative to the shape of the artery in the absence of the device.

Further typically, the device causes an increase in the strain in at least a portion of the arterial wall, relative to the strain in the arterial wall in the absence of the device, without substantially affecting blood flow through the artery. For example, the rate of blood flow through the artery in the presence of device 100 may be more than 70 percent, e.g., more than 90 percent of the blood flow in the absence of the device.

For some applications, an insubstantial effect on flow is achieved by maintaining an internal diameter of the artery, in the presence of the device, that is at least 30 percent of the diameter of the artery, in the absence of the device, throughout the cardiac cycle. Alternatively or additionally, an insubstantial effect on flow is achieved by maintaining the cross sectional area of the artery, in the presence of the device, to be at least 20 percent of the sectional area, in the absence of the device, at a given stage in the subject's cardiac cycle.

For some applications, the flow through the artery to which the device is coupled is monitored during the implantation of the device, and the device is configured to not reduce the flow by more than 15 percent. For some applications, the degree of force applied to the artery, and/or a physical distance between parts of the device, is modulated until the measured flow is not reduced by more than 15 percent. For some applications the absolute minimal distance across the artery is limited to no less than 1.5 mm.

For some applications, the extravascular devices contact the artery around which they are placed along a length of 5 mm.

For some applications, an extravascular device is used that is in accordance with one or more of the devices described in U.S. patent application Ser. No. 12/602,787 to Gross, which is incorporated herein by reference.

For some applications, a plurality of extravascular devices 100 are placed around the artery, as shown in FIG. 9D. For some applications, the plurality of extravascular devices are coupled to each other by a coupling element 105. The extravascular devices are typically spaced from each other such that there are non-contact regions 103 between each of the extravascular devices. Each of the non-contact regions is contiguous and, typically, has a length L1 of more than 0.5 mm (e.g., more than 2 mm), and/or less than 8 mm (e.g., less than 6 mm). For example, length L1 may be 0.5-8 mm, e.g., 2-6 mm. The arterial wall is typically able to pulsate at the non-contact regions.

Figure 10:
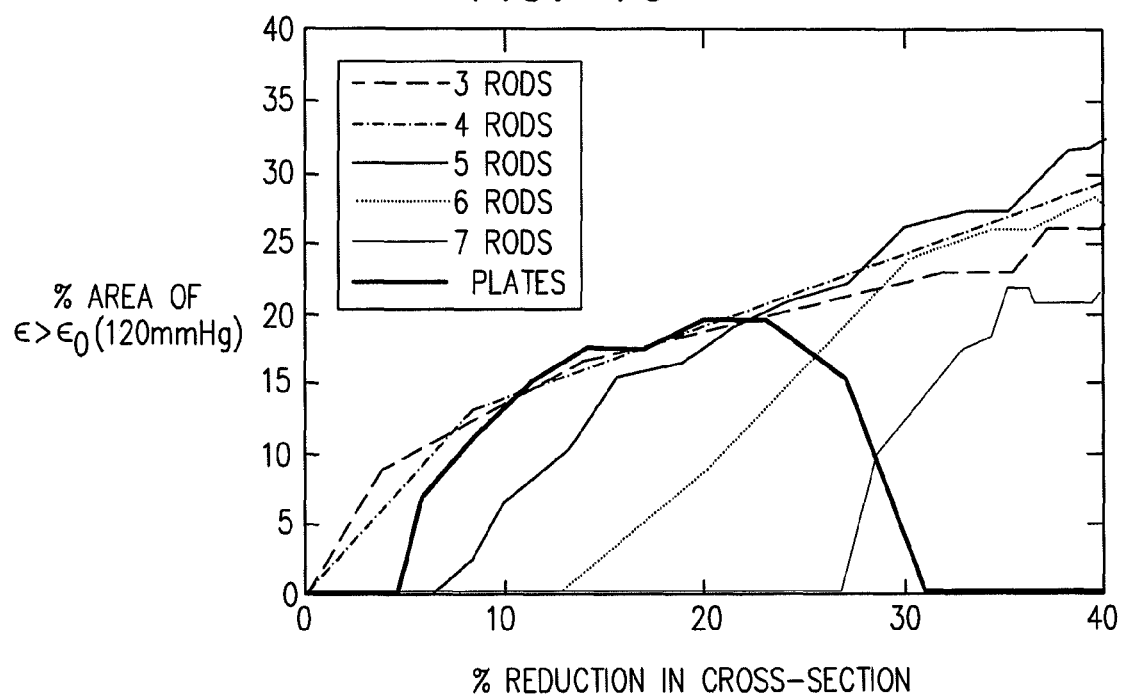
FIG. 10 is a graph that indicates the portion of an arterial wall having a strain that is greater than a threshold value, as a function of the reduction in the cross-sectional area of the artery, for respective extravascular devices, in accordance with some applications of the present invention.

Reference is now made to FIG. 10, which is a graph generated by computer simulation, which indicates the circumferential portion of an arterial wall having a strain that is greater than a threshold value, as a function of the reduction in the cross-sectional area of the artery, for respective extravascular devices. For some applications of the present invention, an extravascular device is placed around an artery, as described hereinabove. Typically, the extravascular device increases strain in at least regions of the arterial wall without substantially reducing the cross-sectional area of the artery, as described hereinabove. Further typically, the extravascular device increases strain in at least regions of the arterial wall without substantially affecting blood flow through the artery, as described hereinabove.

The graph shows several lines, the lines corresponding to extravascular devices that are similar to the extravascular device described hereinabove with reference to FIGS. 3 and 9A. The lines correspond to extravascular devices that have, respectively, three, four, five, six, and seven contact regions with the arterial wall around the circumference of the artery. In addition, one of the lines corresponds to two flat plates that are placed against the outer surface of the artery.

The simulation was generated for an artery at 100 mmHg of pressure. When the extravascular devices herein are placed on the arterial wall, the strain in at least some portions of the arterial wall is increased. Placing the extravascular devices on the arterial wall typically reduces the cross-sectional area of the artery. For a given device, the more the device compresses the artery, the greater the increase in the strain in the arterial walls, and the greater the reduction in the cross-sectional area of the artery.

The x-axis of the graph of FIG. 10 indicates the reduction in the cross-sectional area of the artery generated by the devices. The y-axis measures the percentage of the circumference of the arterial wall having a strain that is at least equivalent to what the strain of the arterial wall would be, if the pressure in the artery were 120 mmHg. Typically, the baroreceptor firing rate in such areas when the pressure is 100 mmHg, during use of the devices described hereinabove, will be generally equivalent to, or greater than the baroreceptor firing rate at 120 mmHg pressure in the absence of use of the devices. Thus, each of the lines in the graph is a measure of the percentage of the circumference of the arterial wall having the increased strain as a function of the reduction in the arterial cross-sectional area that is necessary to induce the increase in strain.

It may be observed that the devices having a smaller number of contact regions with the artery are typically more effective at increasing the strain in the arterial wall by applying a compression force that does not substantially reduce the cross-sectional area of the artery. For example, devices having three and four contact regions with the artery increase the strain of, respectively, 13 percent and 14 percent of the arterial wall to the equivalent of 120 mmHg of pressure while only reducing the cross-sectional area of the artery by 10 percent. Typically, a 10 percent reduction in the cross-sectional area of the artery does not substantially reduce blood flow through the artery in a manner that has significant adverse physiological effects.

The inventors hypothesize that the devices having a larger number of contact regions with the artery are less effective at increasing the strain in the arterial wall than those with a smaller number of contact regions, because the device acts to support the arterial wall at the contact regions, thereby reducing pulsation of the arterial wall over the course of the cardiac cycle. For this reason, the inventors hypothesize that, at low pressures, the two plates are relatively effective at increasing the strain in the arterial wall, since there is a small amount of contact between the plates and the wall. However, at higher compressive forces, the plates provide more support to the wall since there is a greater contact area between the plates and the wall. Therefore, the plates limit the pulsation of the wall by an increasing amount. At higher compressive forces, the decrease in baroreceptor stimulation due to the reduced pulsation of the artery overrides the increase in baroreceptor stimulation due to the plates exerting pressure on the arterial wall. Thus, at higher compressive forces, the plates are not as effective as the other extravascular devices at increasing the strain in regions of the arterial wall. Nevertheless, the scope of the present invention include the use of such plates, e.g., when strain increase is not the only parameter of importance in selecting an implant.

It is additionally noted that for a broad range of allowed reductions in cross-section, e.g., about 17-30 percent, 3-6 contact regions all function generally well. Thus, at higher compression forces (i.e., by reducing the cross-sectional area of the artery by a greater amount), the devices having a greater number of contact regions with the artery become more effective at increasing the strain in the arterial wall. For example, by reducing the cross-sectional area of the artery by 30 percent, each of the devices having three to six contact regions with the artery increases the strain of between 22 percent and 26 percent of the arterial wall to the equivalent of 120 mmHg of pressure.

Figure 11:
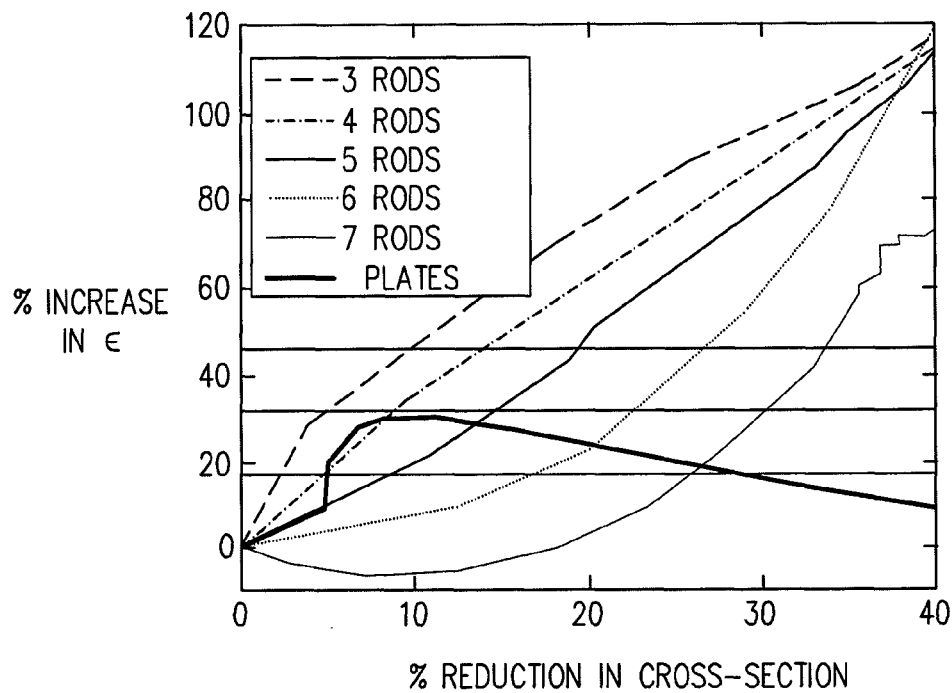
FIG. 11 is a graph showing the maximum percentage increase in the strain of the arterial wall as a function of the reduction in the cross-sectional area of the artery, for respective extravascular devices, in accordance with some applications of the present invention.

Reference is now made to FIG. 11, which is a graph showing the maximum percentage increase in the strain of the arterial wall as a function of the reduction in the cross-sectional area of the artery, for respective extravascular devices.

The graph shows several lines, the lines corresponding to extravascular devices that are similar to the extravascular device described hereinabove with reference to FIGS. 3 and 9A. The lines correspond to extravascular devices that have, respectively, three, four, five, six, and seven contact regions with the arterial wall around the circumference of the artery. In addition, one of the lines corresponds to two plates that are placed against the outside surface of the artery.

The simulation was generated for an artery at 100 mmHg of pressure. The bottom, middle, and top horizontal lines correspond, respectively, to the maximum strain in the vessel wall at 120 mmHg, 140 mmHg, and 160 mmHg pressure, when no device is placed on the artery. When the devices herein are placed on the arterial wall, the maximum strain of the arterial wall is increased. Placing the devices on the arterial wall typically reduces the cross-sectional area of the artery. For a given device, the more the device compresses the artery, the greater the maximum strain in the arterial walls, and the greater the reduction in the cross-sectional area of the artery.

The x-axis of the graph of FIG. 11 measures the reduction in the cross-sectional area of the artery generated by the devices. The y-axis measures the maximum strain in the arterial wall.

It may be observed that for the devices for which the data shown in the graph was generated, the fewer the number of contact regions that the device made with the arterial wall, the more effective the device is at increasing the maximum strain in the arterial wall for a given reduction in the cross-sectional area of the artery that is caused by the device. For example, by compressing the artery such that it has a 20 percent reduction in its cross-sectional area:

the device having three contact regions generates a maximum increase of 75 percent in the arterial wall strain, the device having four contact regions generates a maximum increase of 62 percent in the arterial wall strain, the device having five contact regions generates a maximum increase of 50 percent in the arterial wall strain, the device having six contact regions generates a maximum increase of 23 percent in the arterial wall strain, and the device having seven contact regions generates a maximum increase of less than 5 percent in the arterial wall strain.

Thus, in accordance with some applications of the present invention, extravascular devices having three or more contact regions (e.g., three to six) with the artery are placed around the outside of the artery. The devices typically provide contact regions and non-contact regions of the arterial wall, as described hereinabove. The devices typically increase the strain in the arterial wall, thereby generating increased baroreceptor firing in the artery.

Figure 12:
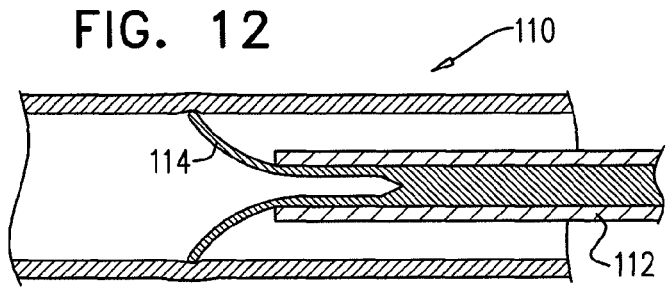
FIG. 12 is a schematic illustration of a device for measuring the baroreceptor response of a subject to pressure that is exerted on the inner wall of an artery of the subject, in accordance with some applications of the present invention.

Reference is now made to FIG. 12, which is a schematic illustration of a device 110 that is used to test the baroreceptor response of a subject to a range of intravascular pressures, in accordance with some applications of the present invention. For some applications, before an intravascular device is inserted into a subject's artery, the baroreceptor response of the subject is tested using measuring device 110. Catheter 112 is inserted into artery 20, in which the intravascular device will be implanted. Extendable arms 114 are extendable from the distal end of the catheter, and are configured such that the pressure that the arms exert on the arterial wall increases, as the portion of the arms that extends from the catheter increases.

Extendable arms 114 are extended incrementally from the distal end of the catheter. At each of the increments, the subject's blood pressure is measured in order to determine the baroreceptor response to the pressure that the arms are exerting on the arterial wall. On the basis of the blood pressure measurements, it is determined which intravascular device should be inserted into the subject's artery, and/or what dimensions the intravascular device should have.

For some applications, a measuring device including arms 114 or a similar measuring device is left in place in the artery, but catheter 112 is removed before the blood pressure measurements are taken. For example, the catheter may be removed in order to increase blood flow through the artery, relative to when the catheter is in place. Once it has been determined, using the measuring device, which intravascular device should be placed inside the artery, and/or what dimensions the intravascular device should have, the measuring device is removed from the artery and the intravascular device is placed inside the artery.

For some applications, a toroid balloon is placed inside the artery and is used as a measuring device. The balloon is inflated incrementally such that the balloon applies varying amounts of pressure to the arterial wall, and the subject's blood pressure is measured in order to measure the response to the pressure being applied to the wall. In this manner, it is determined which intravascular device should be used, and/or what dimensions the intravascular device should have. During the aforementioned measuring procedure, blood continues to flow through the artery, via a central hole in the toroid balloon.

For some applications, the intravascular devices described herein are inserted to an implantation site inside or (using a non-transvascular route) outside of the subject's artery, while the device is in a first configuration thereof. When the device has been placed at the implantation site, the configuration of the device is changed to a second configuration, in which the device is effective to increase baroreceptor stimulation, in accordance with the techniques described herein. For example, the device may be made of nitinol, or another shape memory material, and the configuration of the device may be changed by applying an RF signal, and/or another form of energy, to the device. For some applications, the device is implanted at an implantation site that is close to the subject's skin, and the RF signal is applied to the device via the subject's skin.

For some applications, devices are applied to the carotid artery of a subject who suffers from carotid sinus hypersensitivity, in order to reduce baroreceptor sensitivity of the carotid sinus, by reducing pulsation of the artery. For example, a device may be placed inside or outside the artery such that the device makes contact with the artery at more than six contact points, and/or over more than 180 degrees of the circumference of the artery. For some applications, a device (e.g., a stent) is placed inside or outside of the artery such that the device makes 270-360 degrees of contact with the artery.

Figure 13:
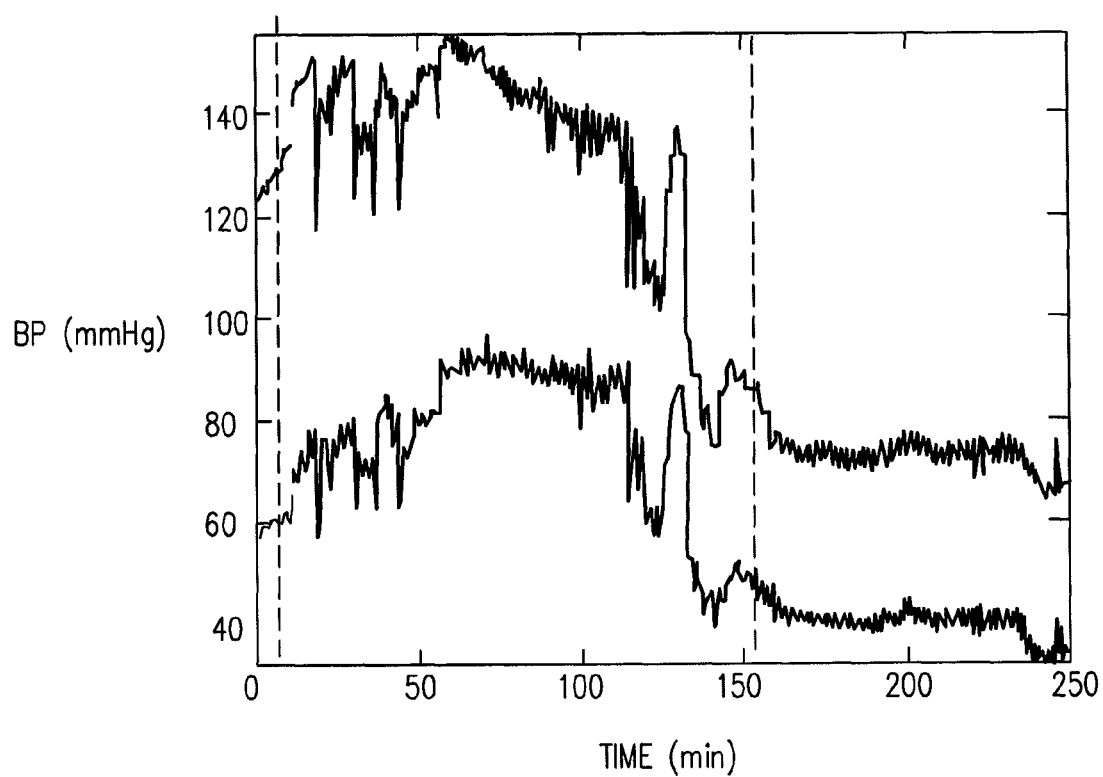
FIG. 13 is a graph showing the blood pressure measured in a dog before and after the insertion of intravascular devices into the dog's carotid sinuses, in accordance with some applications of the present invention.

Reference is now made to FIG. 13, which is a graph showing blood pressure measured in a dog, before, during and after the bilateral placement of intravascular devices into the dog's carotid sinuses, in accordance with some applications of the present invention. Intravascular devices which made contact with the carotid sinus at four contact regions (the devices being generally as shown in FIGS. 7A-B) were placed in the dog's left and right carotid sinuses. The beginning and end of the implantation period is indicated in FIG. 13 by, respectively, the left and right vertical dashed lines at about five minutes and 153 minutes.

It may be observed that the implantation of the devices in both sinuses resulted in the dog's systolic blood pressure dropping from above 120 mmHg to below 80 mmHg, and in the dog's diastolic blood pressure dropping from about 60 mmHg to about 40 mmHg. During the implantation procedure the dog's blood pressure rose. The inventors hypothesize that the rise in blood pressure is due to catheters blocking the flow of blood to the carotid arteries during the implantation, resulting in reduced baroreceptor stimulation during the implantation procedure. It is noted that the placement of the device in the dog's sinuses did not have a substantial effect in the dog's heart rate.

Figure 14:
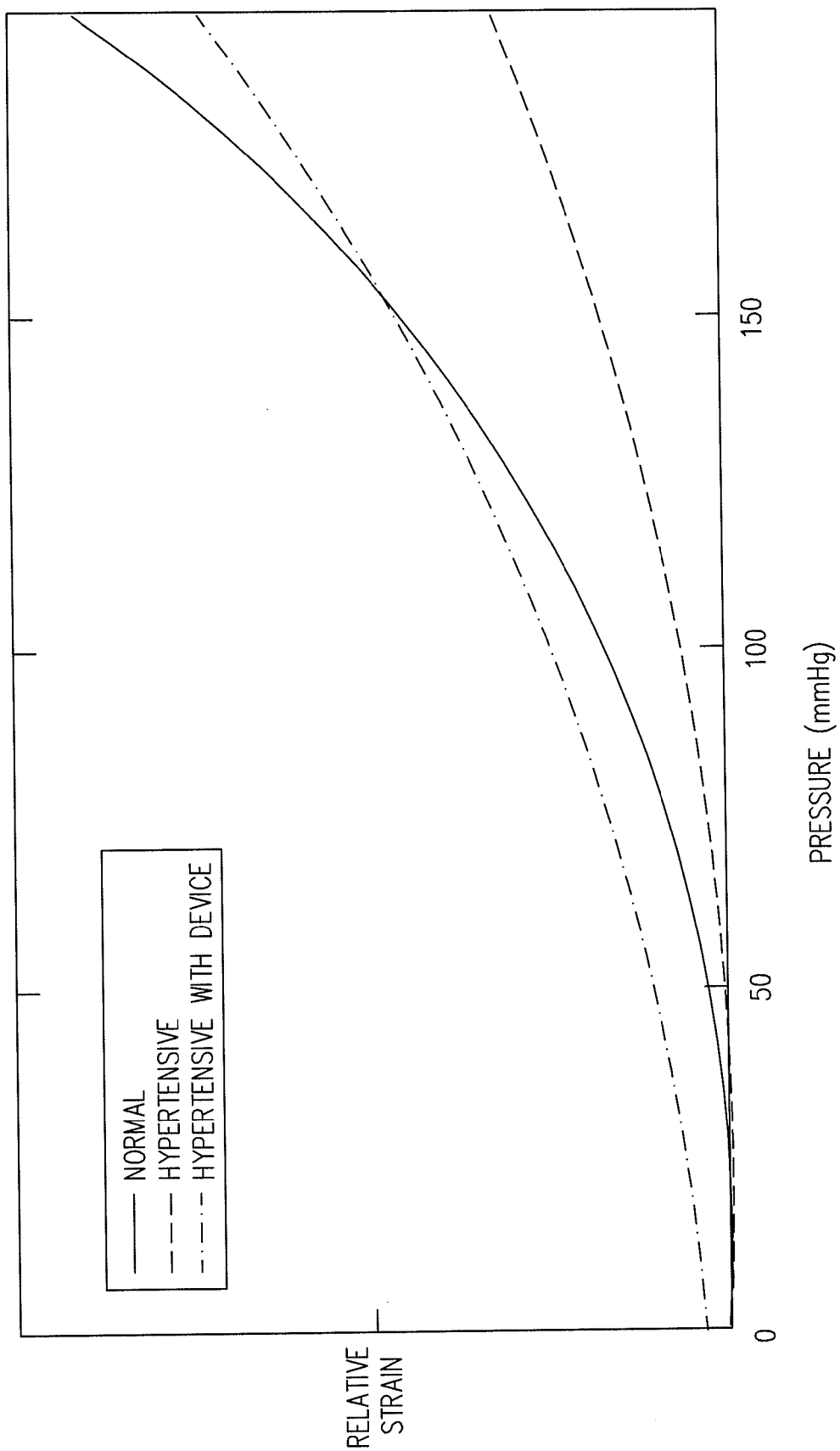
FIG. 14 is a graph showing the pressure-strain curve of the artery of a healthy subject, a hypertensive subject, and a hypertensive subject that uses a device as described herein, in accordance with some applications of the present invention.

Reference is now made to FIG. 14, which is a graph showing the pressure-strain curve of an artery of a normal subject, a hypertensive subject, and a hypertensive subject who uses one of the devices described herein. One of the causes of hypertension is that the arterial wall of the subject does not experience as much strain at any given pressure, as the arterial wall of a normal subject. Thus, the pressure-strain curve of the hypertensive subject is flattened with respect to that of a healthy subject and the strain response is shifted to higher pressures.

The devices described herein increase the strain in the arterial wall at all pressure levels within the artery. For some applications, as shown, at increasing arterial pressures, the absolute increase in the strain in the arterial wall caused by the device increases, relative to the strain experienced by the hypertensive subject before implantation of the device. Thus, the devices described herein both shift the pressure-strain curve of a hypertensive subject upwards and increase the gradient of the curve. A device is typically selected such that the subject's pressure-strain curve, subsequent to implantation of the device, will intersect the normal pressure-strain curve at a pressure of between 80 mmHg and 240 mmHg.

Figure 15A:
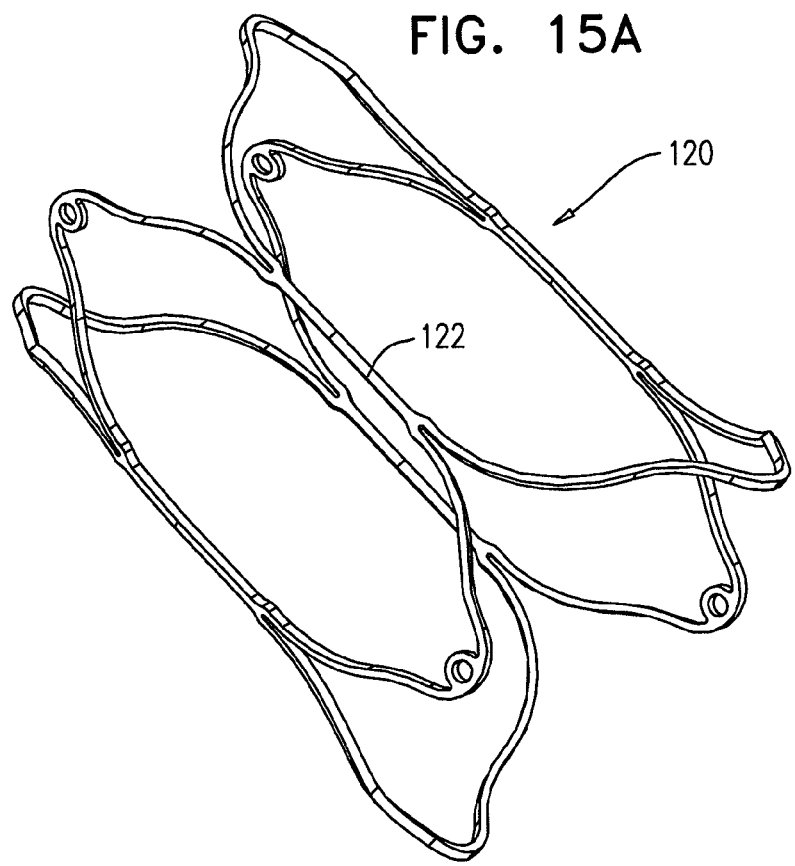
FIGS. 15A-B are schematic illustrations of a device for placing in a subject's artery, in accordance with some applications of the present invention.
Figure 15B:
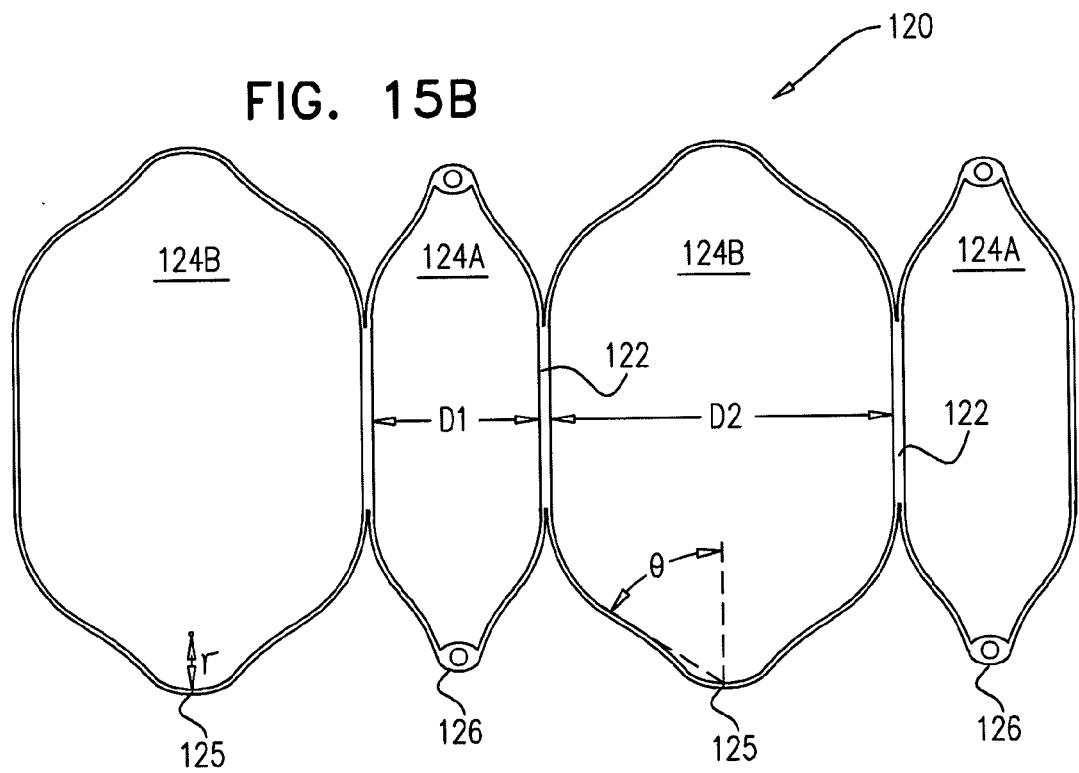

Reference is now made to FIGS. 15A-B, which are schematic illustrations of a device 120 for placing in artery 20, in accordance with some applications of the present invention. Device 120 is generally similar to the intra-arterial devices described hereinabove, except for the differences described hereinbelow. FIG. 15A shows a three-dimensional view of device 120, as the device is shaped when the device is inside the artery, and FIG. 15B shows a flattened, opened, profile of device 120. Device 120 is generally similar to device 80 described hereinabove with reference to FIGS. 7A-B. Device 120 contacts the wall of the artery at four contact regions 122 (which comprise strut portions), thereby flattening the non-contact regions of the artery that are between the contact regions. For some applications, device 120 includes radiopaque markers 126 at proximal and distal ends of the device (as shown) or at other portions of the device.

As shown in FIG. 15B, each of the strut portions is generally spaced from its two adjacent strut portions by respective distances D1 and D2, D1 being smaller than D2. Thus, the device defines a first set of two sides 124A, having widths D1, and a second set of two sides 124B, having widths D2. Placement of device 120 inside artery 20 typically results in the artery having a cross-sectional shape that is more rectangular than in the absence of the device, the cross-sectional shape having sides with lengths D1 and D2. Each of the sides of the cross-sectional shape is supported by a respective side 124A or 124B of device 120. Typically, the ratio of distance D2 to distance D1 is greater than 1:1, e.g., greater than 2:1, and/or less than 5:1, e.g., between 1.1:1 and 5:1 (e.g., between 1.5:1 and 3:1).

Typically, at the distal and proximal ends of device 120, the device is shaped to define crimping arches 125. During transcatheteral insertion of the device into the subject's artery, the device is crimped about the crimping arches, such that the span of the device is reduced relative to the span of the device in its expanded state. Upon emerging from the distal end of the catheter, the device expands against the arterial wall.

For some applications, each crimping arch 125 has a radius of curvature r that is less than 6 mm (e.g., less than 1 mm), in order to facilitate crimping of device 120 about the crimping arch. For some applications, each crimping arch has a radius of curvature r that is greater than 0.3 mm, since a crimping arch having a smaller radius of curvature may damage the arterial wall. Furthermore, when the expanded device exerts pressure on the arterial wall, much of the pressure that is exerted on the device by the arterial wall is resisted by the crimping arches. Therefore, for some applications, each crimping arch has a radius of curvature that is greater than 0.3 mm, in order to facilitate resistance to the pressure that is exerted on the device at the crimping arches. Therefore, for some applications, each crimping arch has a radius of curvature that is 0.3-0.6 mm.

For some applications, the thickness of the struts of device 120 at the crimping arches is greater than the thickness of the struts at other portions of the device, in order to facilitate resistance to the pressure that is exerted on the device at the crimping arches. For some applications, there are additional regions of the struts that are susceptible to absorbing much of the pressure that is exerted on the device by the arterial wall, and the thickness of the struts at the additional regions is greater than the thickness of the struts at other portions of the device.

Figure 15C:
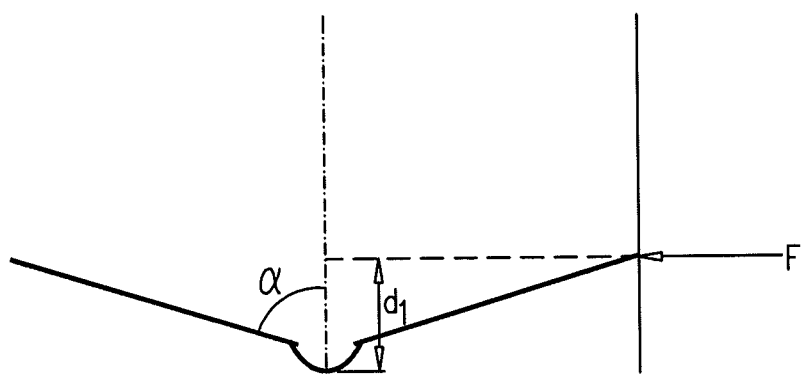
FIGS. 15C-D are schematic illustrations of an arterial wall exerting a force on struts of a device, in accordance with some applications of the present invention.
Figure 15D:
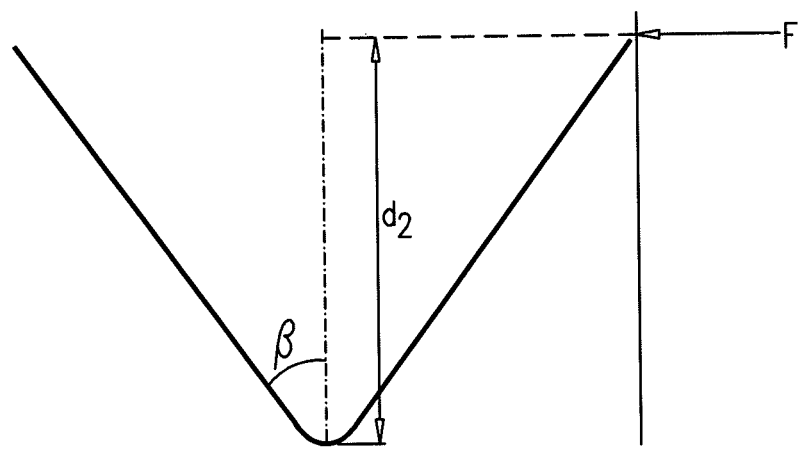

Typically, the strut portions of device 120 project outwardly from crimping arch 125 at an angle theta, angle theta being greater than 30 degrees, e.g., greater than 60 degrees, or greater than 75 degrees. Typically, the outward projection of the struts from the crimping arch at such an angle reduces the moment that the arterial wall exerts about the crimping arch, relative to if the struts projected outwardly from the crimping arch at a smaller angle. This is demonstrated with reference to FIGS. 15C-D, which show a force F of the arterial wall being exerted on struts that project outwardly, respectively, at angles of alpha and beta, alpha being greater than beta. In FIG. 15C, the force is exerted on the strut at a distance d1 from the crimping arch, and in FIG. 15D, the force is exerted on the strut at a distance d2 from the crimping arch, d1 being less than d2. Therefore, the moment that is exerted about crimping point 125 for the strut shown in FIG. 15C is less than that of FIG. 15D.

Figure 16A:
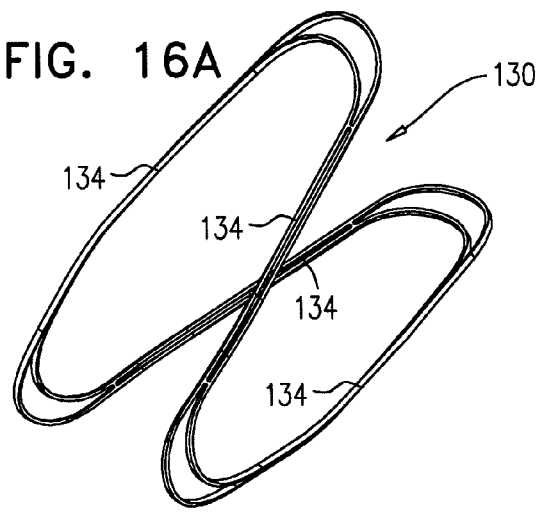
FIGS. 16A-D are schematic illustrations of another device for placing in a subject's artery, in accordance with some applications of the present invention.
Figure 16B:
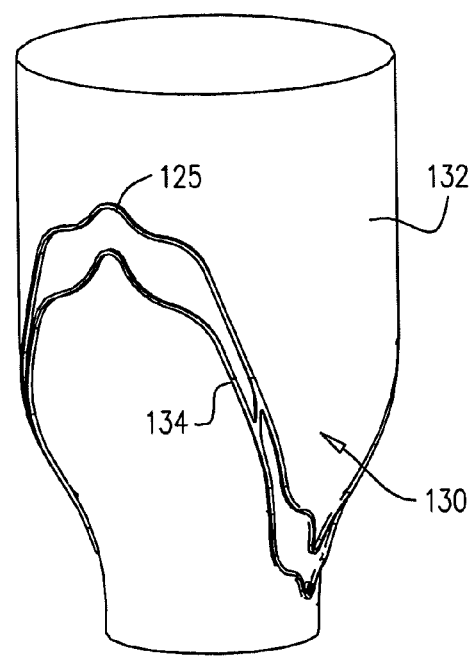
Figure 16C:
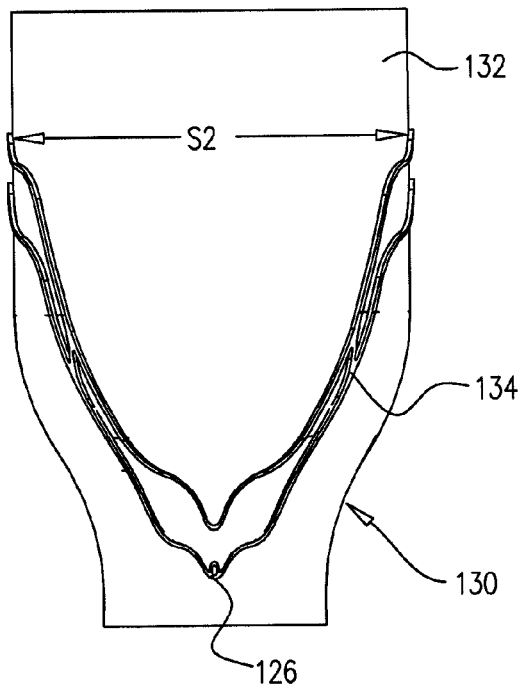
Figure 16D:
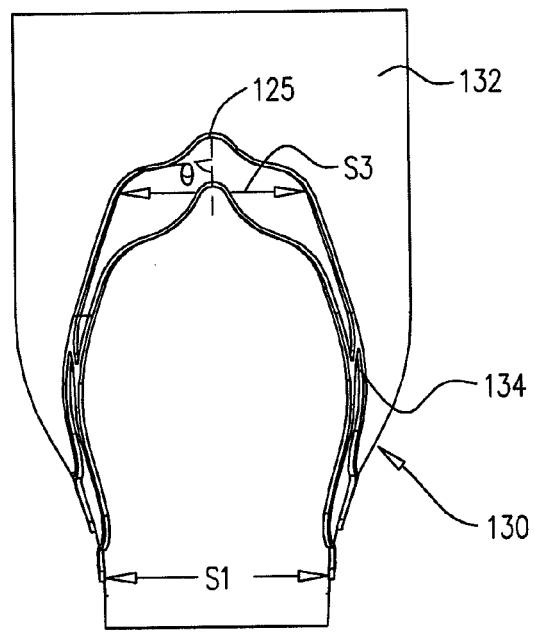

Reference is now made to FIGS. 16A-D, which are schematic illustrations of another device 130 for placing in artery 20, in accordance with some applications of the present invention. Device 130 is generally similar to the intra-arterial devices described hereinabove, except for the differences described hereinbelow. FIGS. 16B-D show device 130 during the shaping of the device, the device typically being placed on a shaping mandrel 132 during the shaping process. As shown, the cross-sectional shape of intra-arterial device 130 varies along the longitudinal axis of the device. Typically, the device defines strut portions 134, all of which diverge from each other, from a first end of the device to the second end of the device. For some applications, each strut portion includes two or more parallel struts, as described hereinbelow.

As shown in FIGS. 16C-D, device 130 is shaped such that at the second end of the device, the device has a greater span S2, than the span of the device S1 at the first end of the device. Typically, the ratio of S2 to S1 is greater than 1:1, e.g., greater than 1.1:1, and/or less than 2:1, e.g., between 1.1:1 and 2:1 (e.g., between 1.1:1 and 1.4:1).

For some applications, devices are inserted into a subject's artery that are shaped differently from device 130, but which are also shaped such that at the second end of the device, the device has a greater span S2, than the span of the device S1 at the first end of the device, for example, as described with reference to FIGS. 18A-D.

Due to the ratio of S2 to S1, upon placement of device 130 inside the artery, the shape of the artery typically becomes increasingly non-circular (e.g., elliptical or rectangular), along the length of the artery, from the first end of the device (having span S1) to the second end of the device (having span S2). Furthermore, due to the ratio of S2 to S1, upon placement of device 130 inside the artery, the cross-sectional area of the artery typically increases along the length of the artery, from the first end of the device (having span S1) to the second end of the device (having span S2). Typically, the device is placed such that the first end of the device (which has the smaller span) is disposed within the internal carotid artery, and the second end of the device (which has the greater span) is disposed at the carotid sinus. In this configuration, the device thus stretches the carotid sinus, due to the span of the device at the second end of the device, but does not substantially stretch the internal carotid artery.

As shown in FIGS. 16C-D, device 130 is shaped such that in the vicinity of the second end of the device, the device has a greater span S2 in a first direction than a span S3 of the device in a second direction. For some applications, the ratio of S2 to S3 is greater than 1:1, e.g., greater than 2:1, and/or less than 5:1, e.g., between 1.1:1 and 5:1 (e.g., between 1.5:1 and 3:1). Typically, the ratio of S2 to S3 enhances flattening of the artery in which device 130 is placed in the direction of span S2.

Typically, device 130 includes three or more diverging strut portions 134, e.g., four diverging strut portions, as shown. For some applications, device 130 includes crimping arches 125 at the ends of the device, the crimping arches being generally similar to crimping arches 125, as described hereinabove with reference to device 120. For some applications, the strut portions of device 130 project outwardly from crimping arches 125 at an angle theta, angle theta being greater than 30 degrees, e.g., greater than 60 degrees, or greater than 75 degrees, in a generally similar manner to that described with reference to device 120. For some applications, each of the strut portions comprises two struts that are translated longitudinally with respect to one another (i.e., the struts are doubled), in order to provide mechanical strength to the struts. Alternatively, each strut portion includes a single strut, or more than two struts that are translated longitudinally with respect to each other.

Figure 17A:
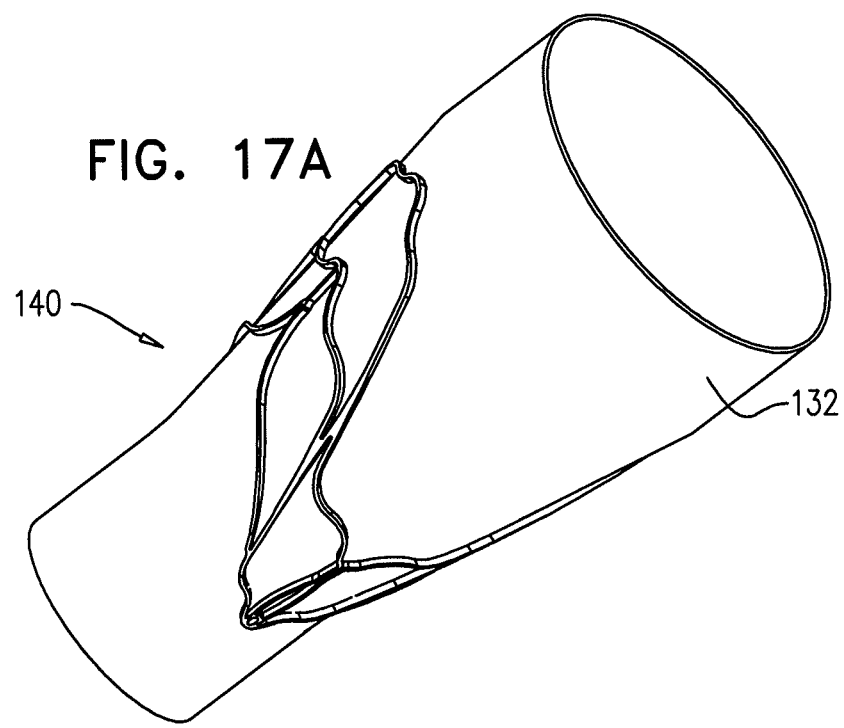
FIGS. 17A-D are schematic illustrations of yet another device for placing in a subject's artery, in accordance with some applications of the present invention.

Reference is now made to FIGS. 17A-D, which are schematic illustrations of yet another device 140 for placing in artery 20, in accordance with some applications of the present invention. Device 140 is generally similar to the intra-arterial devices described hereinabove, except for the differences described hereinbelow. FIG. 17A shows device 140 during the shaping of the device, the device typically being placed on shaping mandrel 132 during the shaping process. As shown, the cross-sectional shape of intra-arterial device 140 varies along the longitudinal axis of the device.

Figure 17B:
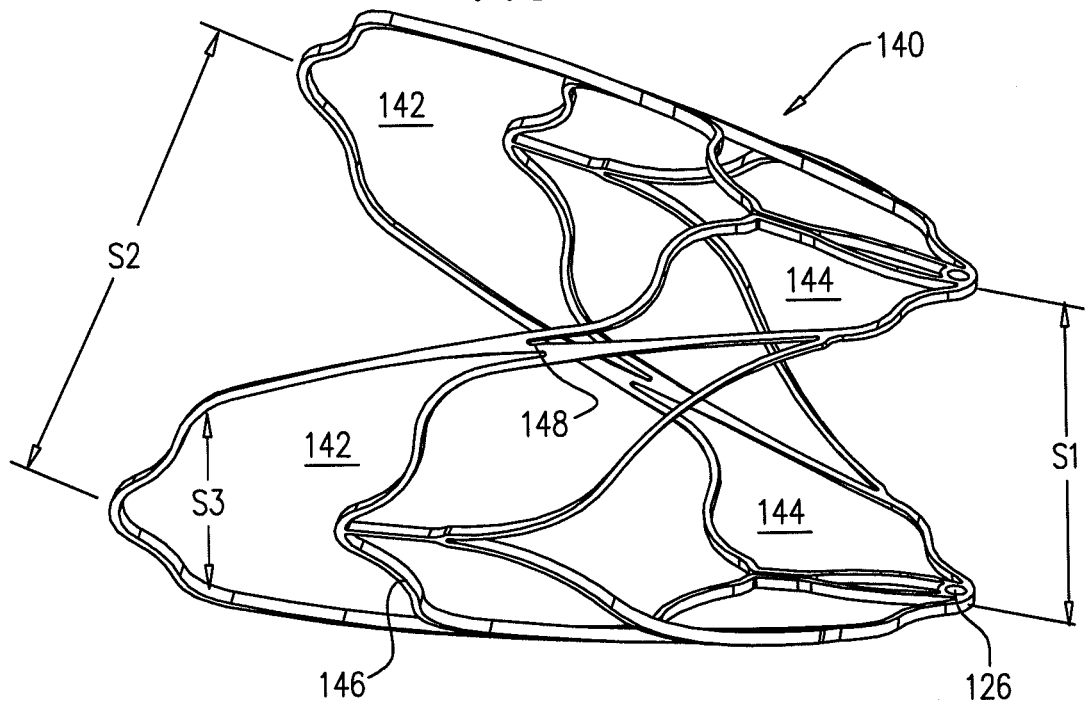

As shown in FIG. 17B, device 140 is shaped such that at the second end of the device, the device has a greater span S2, than the span of the device S1 at the first end of the device. Typically, the ratio of S2 to S1 is greater than 1:1, e.g., e.g., greater than 1.1:1, and/or less than 2:1, e.g., between 1.1:1 and 2:1 (e.g., between 1.1:1 and 1.4:1).

Due to the ratio of S2 to S1, upon placement of device 140 inside the artery, the shape of the artery typically becomes increasingly non-circular (e.g., elliptical or rectangular), along the length of the artery, from the first end of the device (having span S1) to the second end of the device (having span S2). Furthermore, due to the ratio of S2 to S1, upon placement of device 130 inside the artery, the cross-sectional area of the artery typically increases along the length of the artery, from the first end of the device (having span S1) to the second end of the device (having span S2). Typically, the device is placed such that the first end of the device (which has the smaller span) is disposed within the internal carotid, and the second end of the device (which has the greater span) is disposed at the carotid sinus. In this configuration, the device thus stretches the carotid sinus, due to the span of the device at the second end of the device, but does not substantially stretch the internal carotid.

Device 140 is shaped to define four sides. Two of the sides, which are opposite to one another, are configured to act as artery contact regions 142 (shown in FIG. 17C), and apply pressure to the walls of the artery by contacting the artery. The other two sides of device 140, which are also opposite to one another, are configured to act as crimping regions 144 (shown in FIG. 17D). During transcatheteral implantation of the device into the artery, the crimping regions facilitate crimping of the device.

It is noted that the sides of device 140 that act as artery contact regions 142 are typically also somewhat crimpable. Typically, as shown, the sides of device 140 that act as artery contact regions 142 include crimping arches 125 (as described hereinabove), which facilitate crimping of the device.

Figure 17C:
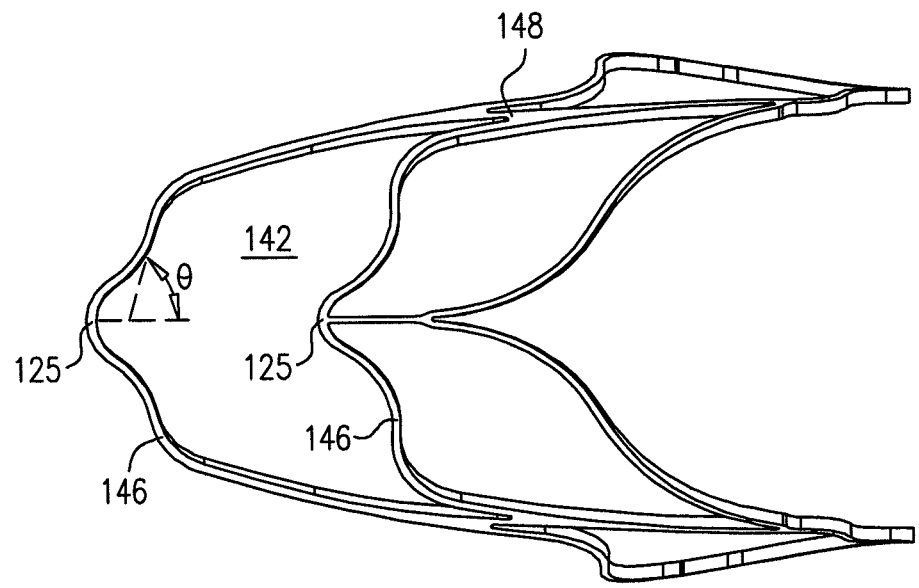

An artery contacting region 142 of device 140 is shown in FIG. 17C. Upon implantation inside an artery, artery contact regions 142 exert pressure on the artery wall, thereby flattening regions of the arterial wall between the artery contact regions, and increasing the strain in the arterial wall at the flattened regions, as described hereinabove. For some applications, the artery contact regions comprise two or more struts 146 that are translated longitudinally with respect to one another. Typically, the struts of a given artery contact region are coupled to one another by a reinforcing element 148. For some applications, the reinforcing element is disposed such that when the artery contact region is crimped, the longitudinal translation of the struts with respect to one another is maintained. For some applications, struts 146 of device 140 project outwardly from crimping arches 125 at an angle theta, angle theta being greater than 30 degrees, e.g., greater than 60 degrees, or greater than 75 degrees, in a generally similar manner to that described with reference to device 120.

Figure 17D:
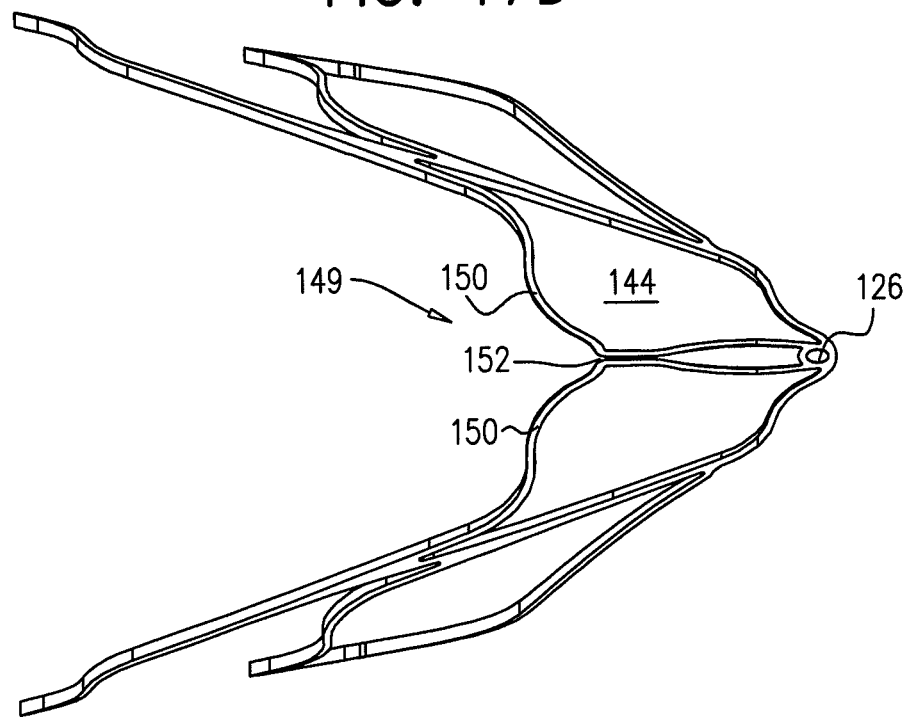

A crimping region 144 of device 140 is shown in FIG. 17D. For some applications, crimping region 144 comprises a locking mechanism 149. During crimping of the device, the locking mechanism is unlocked, to facilitate crimping of the device. When the device is implanted into artery 20, the locking mechanism is locked, so as to prevent the crimping regions from becoming crimped due to pressure that is exerted on the device by the artery. For example, the locking mechanism may comprise two struts 150 that are shaped so as to become locked in placed with respect to one another at a locking interface 152. In order to crimp the device, one of the struts is forced above or below the plane of the locking interface. The struts are pre-shaped, such that when the struts are not locked with respect to one another, the struts move toward one another, such that the struts at least partially overlap with one another. Alternatively or additionally, other locking mechanisms are used. For example, a hinged-based mechanism may be used.

Reference is now made to FIGS. 18A-B, which are schematic illustrations of respective sides 124A and 124B of device 120 for placing in artery 20, in accordance with some applications of the present invention. Device 120 is generally as described hereinabove with reference to FIGS. 15A-B, except that device 120 as shown in FIGS. 18A-B is shaped such that at the second end of the device, the device has a greater span S2, than the span of the device S1 at the first end of the device. Typically, the ratio of S2 to S1 is greater than 1:1, e.g., e.g., greater than 1.1:1, and/or less than 2:1, e.g., between 1.1:1 and 2:1 (e.g., between 1.1:1 and 1.4:1).

Figure 18C:
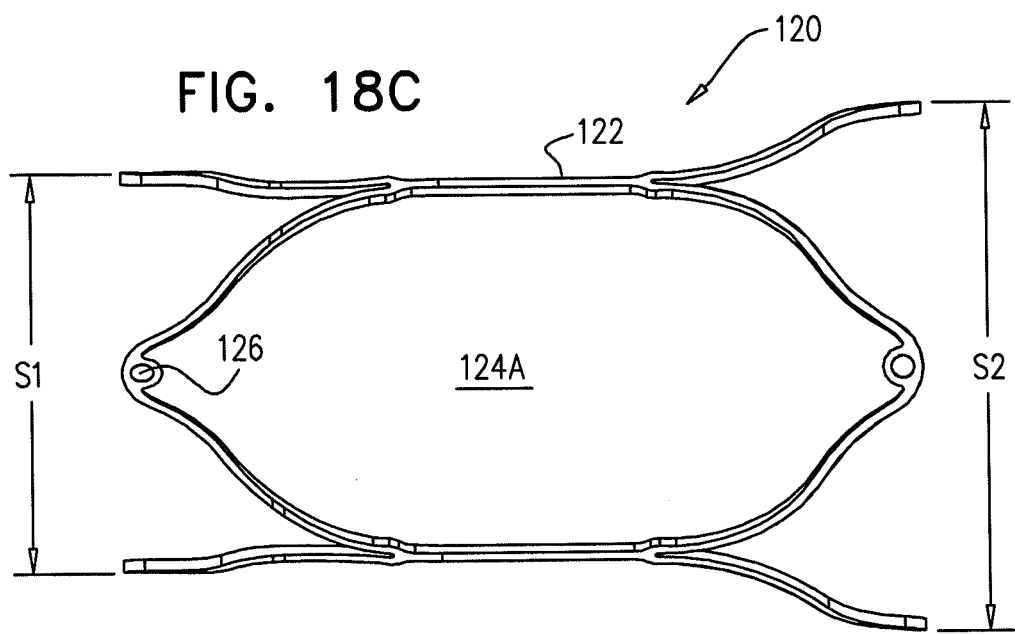
Figure 18D:
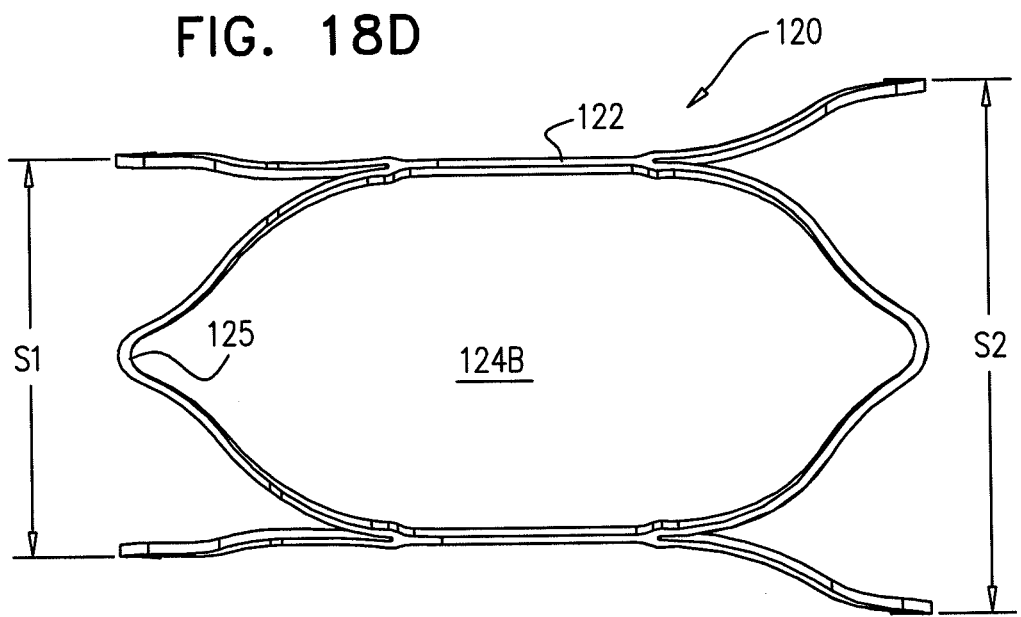

Reference is now made to FIGS. 18C-D, which are schematic illustrations of respective sides 124A and 124B of device 120 for placing in artery 20, in accordance with some applications of the present invention. Device 120 is generally as described hereinabove with reference to FIGS. 15A-B and FIGS. 18A-B, except that device 120 as shown in FIGS. 18C-D is shaped such that (a) sides 124A and 124B are of equal widths, and (b) at the second end of the device, the device has a greater span S2, than the span of the device S1 at the first end of the device. For some applications, a device is used that defines four parallel artery contact regions 122, all of which are separated from adjacent artery contact regions by an equal distance, as shown in FIGS. 18C-D.

Typically, the ratio of S2 to S1 of device 120 as shown in FIGS. 18C-D is as described hereinabove. Thus, the ratio of S2 to S1 is typically greater than 1:1, e.g., e.g., greater than 1.1:1, and/or less than 2:1, e.g., between 1.1:1 and 2:1 (e.g., between 1.1:1 and 1.4:1).

Figure 19:
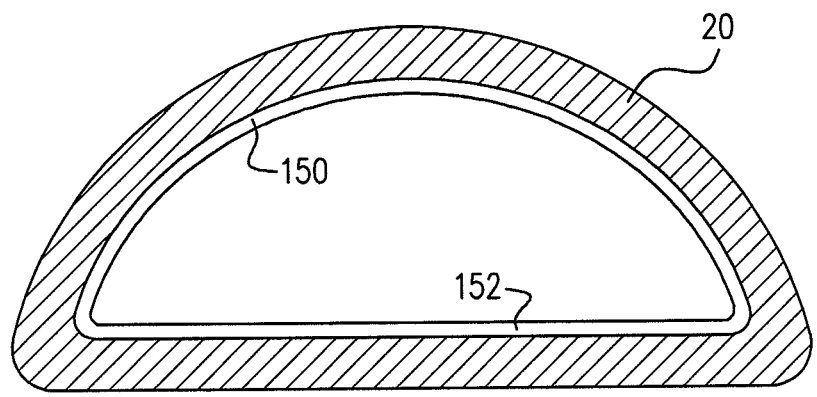
FIG. 19 is a schematic illustration of a device having a D-shaped cross-section for placing in a subject's artery, in accordance with some applications of the present invention.

Reference is now made to FIG. 19, which is a schematic illustration of a D-shaped device 150 for placing inside artery 20, in accordance with some applications of the present invention. For some applications, a device having a D-shaped cross-section, as shown, is placed inside the artery. A straight portion 152 of the cross-sectional shape flattens a portion of the arterial wall that is adjacent to the straight portion, thereby increasing the strain in the portion of the arterial wall relative to the strain in the portion of the arterial wall in the absence of the device.

It is noted that device 120 and other intra-arterial devices described herein (such as devices 70, 80, and 90) define contact regions that contact the intra-arterial wall, the contact regions comprising a plurality of generally parallel strut portions. Typically, for each of the devices, the minimum distance between a first strut portion of the device and an adjacent strut portion to the first strut portion, is 2 mm. It is further noted that the intra-arterial devices described herein (such as devices 60, 70, 80, 90, 120, 130 140, and 150) cause the artery to assume a non-circular cross-sectional shape, such as a triangular, a rectangular, or an oval shape.

For some applications, the intra-arterial devices described herein (such as devices 60, 70, 80, 90, 120, 130, 140, and 150) are shaped to define struts, or other artery contact regions, that are configured to change a shape of the arterial wall, by exerting a force on the arterial wall. The devices additionally include a mesh in between the regions that are configured to change the shape of the arterial wall. The mesh is configured not to change the mechanical behavior of the artery (e.g., by changing the shape of the arterial wall), but is configured to prevent strokes caused by embolization of arterial plaque, by stabilizing the arterial plaque, in a generally similar manner to a regular stent. In general, for some applications, the intra-arterial described herein are used to treat hypertension, and are additionally used to treat arterial disease. For some applications, the intra-arterial devices described herein are placed in a subject's carotid artery subsequent to, or during, a carotid endarterectomy procedure.

For some applications, the intra-arterial devices described herein (such as devices 60, 70, 80, 90, 120, 130, 140, and 150) are configured, upon implantation of the device inside the artery, to cause one or more contiguous portions of the arterial wall to become flattened, each of the contiguous portions having an area of more than 10% of the total surface area of the artery in the region in which the device is placed. Typically, the aforementioned devices contact less than 20 percent (e.g., less than 10 percent) of the wall of the artery at any longitudinal location along the artery. As described hereinabove, for some applications, the intravascular devices described herein (such as devices 60, 70, 80, 90, 120, 130, 140, and 150) have a total cross-sectional area of less than 5 sq mm, e.g., less than 0.8 sq mm, or less than 0.5 sq mm. (The total cross-sectional area should be understood to refer to the cross-sectional area of the solid portions of the devices, and not the space in between the solid portions.) The devices typically have this cross-sectional area over a length of the device of more than 4 mm, e.g., more than 6 mm, and/or less than 12 mm, e.g. less than 10 mm. For example, the devices may have the aforementioned cross sectional area over a length of 4 mm-12 mm, e.g., 6 mm-10 mm, or over a length of 10 mm-30 mm.

For some applications, the dimensions of the intra-arterial devices described herein (such as devices 60, 70, 80, 90, 120, 130, 140, and 150) are chosen based upon patient-specific parameters.

For some applications, the intra-arterial devices described herein (such as devices 60, 70, 80, 90, 120, 130, 140, and/or 150) are made of a shape-memory alloy, such as nitinol. The nitinol is configured to assume an open, deployed configuration at body temperature, and to assume a crimped configuration in response to being heated or cooled to a temperature that differs from body temperature by a given amount, such as by 5 C. In order to insert the device, the device is heated or cooled, so that the device assumes its crimped configuration. The device is placed inside the artery, and upon assuming body temperature (or a temperature that is similar to body temperature), the device assumes its deployed, open configuration. Subsequently, the device is retrieved from the artery by locally heating or cooling the region of the artery in which the device is disposed. The device assumes its crimped configuration and is retrieved from the artery using a retrieval device. For some applications, a device is inserted into the artery temporarily in order to cause the artery to undergo a permanent shape change. Subsequent to changing the shape of the artery, the device is retrieved from the artery, for example, in accordance with the techniques described above.

For some applications, the intra-arterial devices described herein (such as devices 60, 70, 80, 90, 120, 130, 140, and/or 150) are configured to expand both radially and longitudinally upon implantation of the device inside the subject's artery.

For some applications, the intra-arterial devices described herein (such as devices 60, 70, 80, 90, 120, 130, 140, and/or 150) are implanted at a subject's carotid bifurcation, via a delivery device. During the implantation of the device, the proximal end of the device is released from the delivery device such that the proximal end of the device is positioned at the start of the bifurcation. Subsequent to the proximal end of the device having been positioned, the distal end of the intravascular device is released from the delivery device. For some applications, prior to releasing the distal end of the device, the effect of the device on baroreceptor firing is measured, and the position of the device is adjusted, in response thereto.

For some applications, the intra-arterial devices described herein (such as devices 60, 70, 80, 90, 120, 130, 140, and/or 150) are configured such that, upon implantation of the device inside artery 20, the shape of the device remains substantially the same for the duration of a cardiac cycle of the subject. Alternatively, the device is configured to flex in response to the subject's cardiac cycle. For some applications the device flexes passively, in response to blood pressure changes in the artery. Alternatively or additionally, the device is actively flexed. For example, the device may include a piezoelectric element, and an inductive charged coil (inside or outside of the subject's body), drives the piezoelectric element to flex.

For some applications, baroreceptors of the subject are activated by driving an electrical current toward the baroreceptors via an intra-arterial device described herein (such as device 60, 70, 80, 90, 120, 130, 140, and/or 150). Thus, the baroreceptors are stimulated both by mechanical shape changes to the artery as a result of the device being placed inside the artery, and via the electrical stimulation of the baroreceptors. For some applications, baroreceptors at least partially adapt to the shape change of the artery due to the placement of intra-arterial device inside the artery, and the baroreceptors fire with a lower firing rate at a given blood pressure, relative to when the device was first implanted. For some applications, in response to the lowered firing rate of the baroreceptors, due to the adaptation of the baroreceptors to the implanted device, electrical stimulation of the baroreceptors is increased.

Figure 20:
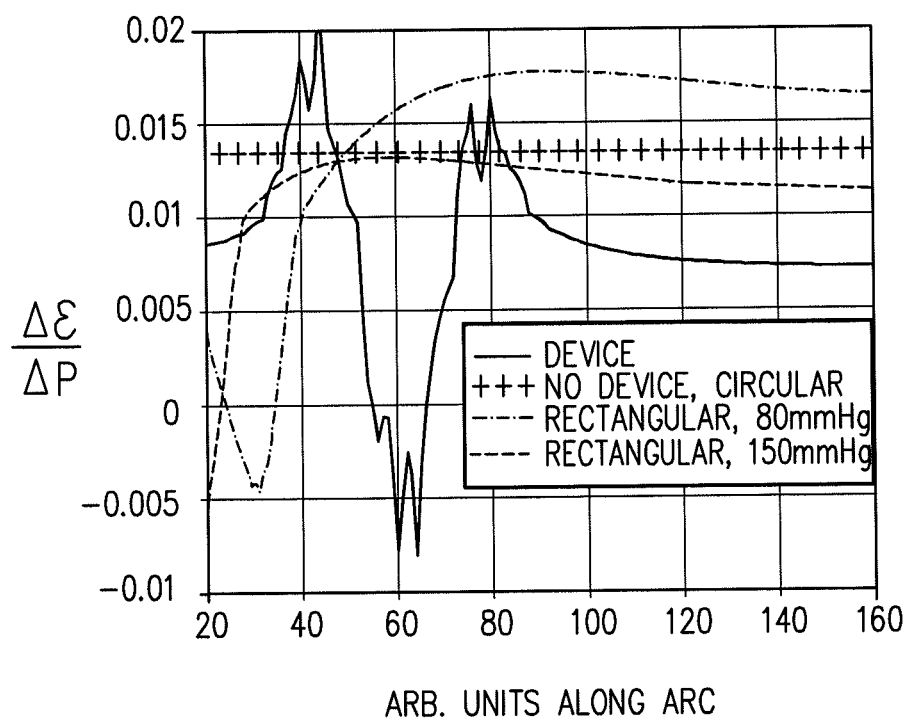
FIG. 20 is a graph showing the derivative of strain versus pressure as a function of rotational position around the artery, in accordance with respective models of an artery, in accordance with some applications of the present invention.

Reference is made to FIG. 20, which is a graph showing the derivative of strain versus pressure as a function of rotational position around the artery, in accordance with respective models of an artery, in accordance with some applications of the present invention. The graph shows the derivative of strain versus pressure as a function of rotational position around a quadrant of an artery, for the following four models of the artery:
1) A circular elastic artery having no device placed therein, at 150 mmHg.
2) An artery having device 120 placed therein, the device causing the artery to assume a rectangular shape. The artery is modeled at a pressure of 150 mmHg. One of the contact points of the device with the artery wall is between 40 and 80 arbitrary units along the x-axis.
3) A rectangular artery without a device placed therein, at 80 mmHg. One of the corners of the rectangle is at 40 and 80 arbitrary units along the x-axis. This model of the artery was generated in order to separate the effect of changing the shape of the artery to a rectangular shape from the effect of having a device (such as device 120) placed inside the artery.
4) The rectangular artery without a device placed therein, at 150 mmHg.

The shapes of the curves indicate the following:
1) As expected, the derivative of the strain with respect to pressure of the circular, elastic artery is constant due to the elasticity of the artery.
2) At the contact point of the intra-arterial device with the artery, the strain-pressure derivative is reduced relative to the rounded artery. At the non-contact regions of the artery, the strain-pressure derivative is also reduced relative to the rounded artery. However, at the non-contact regions, the pressure-strain derivative is still approximately half that of the rounded artery. This indicates that at the non-contact regions, the pulsatility of the artery is reduced, relative to a rounded artery, but that the artery is still substantially pulsatile. Therefore, for some applications, devices are inserted into an artery which re-shape the arterial wall, such that at any longitudinal point along the artery there are non-contact regions at which regions there is no contact between the device and the arterial wall, such that the artery is able to pulsate.
3) Based on the two rectangular models of the artery (at 80 mmHg and 150 mmHg), it may be observed that at the straightened regions of the artery (i.e., not at the corner of the rectangle), the strain-pressure derivative of the artery increases at low-pressures (e.g., 80 mmHg), relative to a rounded, elastic artery. At higher pressures (e.g., 150 mmHg), the strain-pressure derivative of the straightened regions of the artery is roughly equal to that of the rounded, elastic artery. This indicates that straightening the wall of the artery, by causing the artery to assume a rectangular or an elliptical shape, may increase the pulsatility of the artery. Therefore, for some applications, devices are inserted into the artery that straighten regions of the arterial wall.

Experimental Data

A number of experiments were conducted by the inventors in accordance with the techniques described herein.

In one experiment, acute unilateral carotid stimulation was applied to a first set of dogs, either the left or right carotid sinus of the dogs of the first set being squeezed between two smooth metal plates for a period of two to five minutes. Acute bilateral carotid stimulation was applied to a second set of dogs, both carotid sinuses of the dogs of the second set being squeezed between two smooth metal plates for a period of 10 to 30 minutes. The mean effect of the unilateral carotid sinus stimulation was to decrease systolic blood pressure by 11 mmHg, and the mean effect of the bilateral stimulation was to decrease systolic blood pressure by 29 mmHg. The results of the bilateral stimulation had a p-value of less than 0.001. These results indicate that using the devices described herein for either unilateral or for bilateral carotid sinus stimulation may be effective at reducing a subject's blood pressure.

In another experiment, two dogs were chronically implanted (for periods of more than two months) with plates that squeezed the carotid sinus, in accordance with the techniques described herein. The dogs had the plates implanted around both carotid sinuses. On a first one of the dogs, the plates became dislodged from one of the sinuses within two days of implantation. The plates remained implanted around both carotid sinuses of the second dog, until the plates were removed. The blood pressure of the dogs was measured, via an implanted telemeter, for two to four weeks before the device implantation. In the first dog, the dog's blood pressure was measured after the implantation of the device for two weeks, and was subsequently terminated, due to a malfunction in the transmission of the telemeter. In the second dog, the dog's blood pressure was measured for six weeks after the implantation of the device.

For the dog that had the plates chronically implanted around only one carotid sinus, the average diastolic blood pressure measured in the dog over two weeks post-implantation was 6 mmHg less than the average diastolic blood pressure measured in the dog over two weeks pre-implantation. The average systolic blood pressure measured in the dog over two weeks post-implantation was 8 mmHg less than the average systolic blood pressure measured in the dog over two weeks pre-implantation.

For the dog that had the plates chronically implanted bilaterally, the average diastolic blood pressure measured in the dog over six weeks post-implantation was 10 mmHg less than the average diastolic blood pressure measured in the dog over two weeks pre-implantation. The average systolic blood pressure measured in the dog over six weeks post-implantation was 18 mmHg less than the average systolic blood pressure measured in the dog over two weeks pre-implantation.

These results indicate that chronic implantation of the devices described herein for either unilateral or for bilateral carotid sinus stimulation may be effective at chronically reducing a subject's blood pressure.

In addition to measuring the blood pressure of the dog that had plates chronically implanted bilaterally around its carotid sinuses, the inventors measured the baroreceptor sensitivity of the dog, for several weeks, both pre-implantation and post-implantation of the device using generally similar techniques to those described in "The effect of baroreceptor activity on cardiovascular regulation," by Davos (Hellenic J Cardiol 43: 145-155, 2002), which is incorporated herein by reference. Pre-implantation of the device, the mean baroreceptor sensitivity was 14±5 sec/mmHg. Post-implantation of the device, the mean baroreceptor sensitivity was 20±8 sec/mmHg. These results indicate that chronic implantation of the devices described herein may be effective at increasing baroreceptor sensitivity.

In a further experiment that was conducted in accordance with the techniques described herein, five human patients had a device placed around either the left or right carotid sinus, subsequent to undergoing endarterectomy procedures. The device was configured to flatten regions of the wall of the carotid sinus, in accordance with techniques described herein. Of the five patients, two were excluded from the study, since these patients were administered atropine, which may have interfered with the results. Of the three patients who were included in the study, the placement of the device in all of the patients resulted in a decrease in both the systolic and diastolic blood pressure of the patient. For the three patients who were included in the study, the placement of the device resulted in a mean decrease in diastolic blood pressure of 8 mmHg (standard deviation 5) and a mean decrease in systolic blood pressure of 22 mmHg (standard deviation 14), relative to the blood pressures before placement of the device. These results indicate that using the devices described herein for carotid sinus stimulation may be effective at reducing a human subject's blood pressure.

The scope of the present invention includes combining the apparatus and methods described herein with those described in US 2008/0033501 to Gross, and/or U.S. patent application Ser. No. 12/602,787 to Gross, both of which applications are incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
    inserting into an artery of a subject, via a catheter, an implantable device that is shaped to define:
        at least four artery-contact regions, the artery-contact regions comprising at least four longitudinal struts, and
        at least two crimping regions each comprising a locking mechanism comprising a crimping arch disposed at an end of at least one of the artery-contact regions, the locking mechanism comprising the crimping arch being configured to prevent the crimping regions from becoming crimped due to pressure from the wall of the artery on the artery-contact regions,
    the insertion being performed by crimping the crimping regions about the crimping arch during insertion of the device, the locking mechanism unlocked during insertion of the device via the catheter;
    advancing the device out of a distal end of the catheter; and
    upon advancing the device out of the distal end of the catheter, stretching a wall of the artery by applying pressure to the arterial wall with the at least four longitudinal struts and by locking the locking mechanism in order to flatten at least four regions of an arterial wall and change the shape of the arterial wall such that the arterial wall has a rectangular cross-sectional shape to modulate baroreceptor activity.

2. The method according to claim 1, wherein the crimping arch has a radius of curvature of less than 0.6 mm to resist pressure from the wall of the artery.

3. The method according to claim 2, wherein the crimping arch has a radius of curvature of more than 0.3 mm.

4. The method according to claim 2, wherein inserting the device comprises inserting the device, struts of the at least four artery-contact regions of the device projecting outwardly from the crimping arch at an angle that is greater than 30 degrees.

5. The method according to claim 4, wherein inserting the device comprises inserting the device, the struts of the at least four artery-contact regions of the device projecting outwardly from the crimping arch at an angle that is greater than 60 degrees.

6. The method according to claim 5, wherein inserting the device comprises inserting the device, the struts of the at least four artery-contact regions of the device projecting outwardly from the crimping arch at an angle that is greater than 60 degrees.

7. The method according to claim 1, wherein inserting the device comprises inserting the device, a maximum span of the device increasing along a direction of a longitudinal axis of the device from a first end of the device to a second end of the device.

8. The method according to claim 7, wherein inserting the device comprises placing the device such that the second end of the device is placed in a carotid sinus of the subject, and the first end of the device is placed in an internal carotid artery of the subject.

9. The method according to claim 7, wherein inserting the device comprises inserting the device, a ratio of the maximum span of the device at the second end of the device to the maximum span of the device at the first end of the device being between 1.1:1 and 2:1.

10. The method according to claim 9, wherein inserting the device comprises inserting the device, a ratio of the maximum span of the device at the second end of the device to the maximum span of the device at the first end of the device is between 1.1:1 and 1.4:1.

11. The method according to claim 1, wherein inserting the device comprises inserting the device, the artery-contact regions of the device each comprising two or more struts that are longitudinally translated with respect to one another.

12. The method according to claim 11, wherein inserting the device comprises inserting the device, the device including a reinforcing element configured to couple the two or more struts to one another, and to maintain the longitudinal translation of the struts with respect to one another when the device is crimped.

13. The method, according to claim 1, wherein inserting the device comprises inserting the device having a total cross-sectional area of less than 5 sq mm.

14. The method according to claim 13, wherein inserting the device comprises inserting the device having a total cross-sectional area of less than 0.5 sq mm.

15. The method according to claim 1, wherein the thickness of the crimping arch is greater than the thickness of the struts of the artery-contact regions to facilitate resistance to pressure exerted from the wall of the artery on the artery-contact regions.

* * * * *

UNITED STATES PATENT AND TRADEMARK OFFICE
CERTIFICATE OF CORRECTION

PATENT NO. : 9,125,732 B2
APPLICATION NO. : 13/030384
DATED : September 8, 2015
INVENTOR(S) : Yossi Gross et al.

It is certified that error appears in the above-identified patent and that said Letters Patent is hereby corrected as shown below:

In the Claims;

Column 30, Line 39, Claim 6, delete "greater than 60" and replace with --greater than 75--

Signed and Sealed this
Twenty-fourth Day of May, 2016

Michelle K. Lee
*Director of the United States Patent and Trademark Office*